United States Patent
Wood et al.

(10) Patent No.: US 10,238,689 B2
(45) Date of Patent: *Mar. 26, 2019

(54) METHODS FOR COMBATING BACTERIAL INFECTIONS BY KILLING PERSISTER CELLS WITH MITOMYCIN C AND/OR CISPLATIN

(71) Applicant: THE PENN STATE RESEARCH FOUNDATION, University Park, PA (US)

(72) Inventors: Thomas Wood, Port Matilda, PA (US); Brian Kwan, State College, PA (US); Nityananda Chowdhury, State College, PA (US)

(73) Assignee: The Penn State Research Foundation, University Park, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/724,998

(22) Filed: Oct. 4, 2017

(65) Prior Publication Data
US 2018/0117083 A1    May 3, 2018

Related U.S. Application Data

(63) Continuation of application No. 15/088,915, filed on Apr. 1, 2016, now Pat. No. 9,801,909.

(60) Provisional application No. 62/143,576, filed on Apr. 6, 2015, provisional application No. 62/276,542, filed on Jan. 8, 2016.

(51) Int. Cl.
| | |
|---|---|
| *A61P 31/04* | (2006.01) |
| *A61K 31/33* | (2006.01) |
| *A61K 31/40* | (2006.01) |
| *A61K 33/24* | (2006.01) |
| *A61K 31/282* | (2006.01) |
| *A61K 31/407* | (2006.01) |

(52) U.S. Cl.
CPC ............ *A61K 33/24* (2013.01); *A61K 31/282* (2013.01); *A61K 31/407* (2013.01); *A61K 31/33* (2013.01); *A61K 31/40* (2013.01); *A61P 31/04* (2018.01); *Y02A 50/473* (2018.01)

(58) Field of Classification Search
CPC ........ A61K 31/282; A61K 31/40; A61P 31/04
USPC .................................................. 514/492, 410
See application file for complete search history.

(56) References Cited

U.S. PATENT DOCUMENTS 9,801,909 B2 * 10/2017 Wood ..................... A61K 33/24

FOREIGN PATENT DOCUMENTS

WO     WO-0215896 A2 *  2/2002   ............. A61K 45/06

OTHER PUBLICATIONS

Joyce et al., "Antimicrobial spectrum on the antitumor agent, cisplatin", The Journal of Antibiotics, vol. 63, No. 8, pp. 530-532 (2010).*

* cited by examiner

*Primary Examiner* — Kevin E Weddington
(74) *Attorney, Agent, or Firm* — Hodgson Russ LLP

(57) ABSTRACT

The present disclosure provides a method for killing persister cells with mitomycin C and/or cisplatin, or derivatives thereof. Recalcitrant infections are difficult to treat due to persister cells, a subpopulation of all bacterial populations that is highly tolerant against all traditional antibiotics since the cells are dormant and antibiotics are designed to kill growing cells. Here, we show that MMC and cisplatin eradicate persister cells through a growth-independent mechanism, cross-linking DNA. We find both agents are effective against both planktonic cultures and highly robust biofilm cultures for a broad range of bacterial species, including commensal *Escherichia coli* K-12 as well as pathogenic species of *E. coli*, *Staphylococcus aureus*, and *Pseudomonas aeruginosa*. In certain approaches cisplatin is superior to MMC.

19 Claims, 10 Drawing Sheets

Specification includes a Sequence Listing.

SEQUENCE LISTING

<160> NUMBER OF SEQ ID NOS: 4

<210> SEQ ID NO 1
<211> LENGTH: 20
<212> TYPE: DNA
<213> ORGANISM: artificial sequence
<220> FEATURE:
<223> OTHER INFORMATION: Primer

<400> SEQUENCE: 1
tattgcacaa tgggcgcaag                                                    20

<210> SEQ ID NO 2
<211> LENGTH: 20
<212> TYPE: DNA
<213> ORGANISM: artificial sequence
<220> FEATURE:
<223> OTHER INFORMATION: Primer

<400> SEQUENCE: 2
acttaacaaa ccgcctgcgt                                                    20

<210> SEQ ID NO 3
<211> LENGTH: 32
<212> TYPE: DNA
<213> ORGANISM: artificial sequence

```
<220> FEATURE:
<223> OTHER INFORMATION: Primer

<400> SEQUENCE: 3
gaacaacaat tactcaatgc ctggcagtat gc                                    32

<210> SEQ ID NO 4
<211> LENGTH: 34
<212> TYPE: DNA
<213> ORGANISM: artificial sequence
<220> FEATURE:
<223> OTHER INFORMATION: Primer

<400> SEQUENCE: 4
ccataagcac caatattctg gataggtgat gagc                                  34
```

METHODS FOR COMBATING BACTERIAL INFECTIONS BY KILLING PERSISTER CELLS WITH MITOMYCIN C AND/OR CISPLATIN

CROSS REFERENCE TO RELATED APPLICATIONS

This application claims priority to U.S. provisional application No. 62/143,576, filed Apr. 6, 2015, and U.S. provisional application No. 62/276,542, filed Jan. 8, 2016, and is a continuation of U.S. patent application Ser. No. 15/088,915, filed Apr. 1, 2016, the disclosures of each of which are incorporated herein by reference.

GOVERNMENT INTEREST STATEMENT

This invention was made with government support under Contract No. W911NF-14-1-0279, awarded by U.S. Army/ARO. The Government has certain rights in the invention.

FIELD

The present disclosure relates generally to treating bacterial infections, and more specifically to treating and eradication of persister cells.

BACKGROUND

There are 17 million new biofilm infections every year in the U.S.A., which lead to 550,000 fatalities (R. Wolcott, S. Dowd, Plast. Reconstr. Surg. 127, 28S (2011), and biofilms are difficult to treat due to the presence of persister cells (K. Lewis, Curr. Top. Microbiol. Immunol. 322, 107 (2008)). Persisters arise due to metabolic inactivity (K. Lewis, PNat. Rev. Microbiol. 5, 48 (2007); Kwan, et al. Antimicrob. Agents Chemother. 57, 1468 (2013); T. K. Wood, et a., Appl. Environ. Microbiol. 79, 7116 (2013)) and are highly tolerant against all traditional antibiotic classes, which are primarily effective against actively growing cells. Bacterial persistence is a non-hereditary phenotype. (W. Bigger, Lancet 244, 497 (1944)) which occurs both stochastically (N. Q. Balaban, et al., Science 305, 1622 (2004) or through environmental influence (Kwan, et al. (2013), N. Möker, et al., J. Bacteriol. 192, 1946 (2010); Y. Hu, et al., Environ. Microbiol., 17, 1275, (2015); T. Dörr, et al. PLoS Biol. 8, e1000317 (2010); N. M. Vega, et al., Nat. Chem. Biol. 8, 431 (2012)) in a small sub-population of all tested bacterial species (K. Lewis, Curr. Top. Microbiol. Immunol. 322, 107 (2008)) (~1% during stationary phase and in biofilm cultures); (K. Lewis, Curr. Top. Microbiol. Immunol. 322, 107 (2008); K. Lewis, Nat. Rev. Microbiol. 5, 48 (2007)). Few distinctly new antibiotics have been discovered recently (Antibiotic discovery and development. T. J. Dougherty, M. J. Pucci, Eds., (Springer, New York, N.Y., 2012), and current antibiotics are ineffective against persister cells. Thus, there is an ongoing and unmet need for improved approaches to treating infections that comprise persister cells. The present disclosure meets this need.

SUMMARY

The present disclosure relates to methods for reducing and/or eradicating bacterial persister cells and/or dormant viable but non-culturable (VBNC) cells. The method generally comprises administering an effective amount of mitomycin C (MMC) or a derivative thereof, or cisplatin or a derivative thereof, or a combination of MMC or a derivative thereof and cisplatin and a derivative thereof, wherein the bacterial persister cells and/or the VBNC cells are reduced or are eradicated. In certain approaches the reduction of persister cells and/or the VBNC cells is greater than reduction achieved using a suitable reference, non-limiting examples of which include one or more values obtained from exposing persister cells and/or or VBNC cells of the same bacterial species to a matched amount of one of ciprofloxacin, ampicillin, or gentamicin. In embodiments the persister cells and/or VBNC cells reduced or eliminated according to this disclosure are resistant to one or more antibiotics. The one or more antibiotics can comprise MMC or cisplatin. In certain implementations the persister cells and/or VBNC cells are present in anaerobic conditions.

Methods of the disclosure are suitable for reducing and/or eradicating pathogenic bacteria of a variety of types, include Gram-negative and Gram-positive pathogenic bacteria. In certain approaches the pathogenic bacteria comprise pathogenic *S. aureus, P. aeruginosa,* or *E. coli.* In certain implementations methods of the disclosure are used to reduce or eliminate a population of bacteria from a wound of an individual, including but not necessarily in a wound comprising pathogenic bacteria that are resistant to one or more antibiotics. In an embodiment, the bacteria are not resistant to MMC or cisplatin. In certain implementations the disclosure reduces or eradicates bacteria in an infection in an individual. The individual may have been previously been diagnosed with a bacterial infection and treated with at least one antibiotic, but the bacterial infection was not cleared by such previous treatment.

In certain implementations the disclosure reduced or eradicates bacteria that are present in a population in biofilm, and/or are in a stationary growth phase. In an embodiment the bacteria are present in a biofilm and are reduced or are eradicated, but the biofilm is not dispersed. In certain approaches the bacteria may be present on an inanimate surface, including but not necessarily limited to a medical device, including but not necessarily limited to implantable or implanted medical devices.

DESCRIPTION OF THE FIGURES

Where asterisks are referred to in relation to the figures of this disclosure they are red asterisks, unless specified otherwise.

Figure 3:
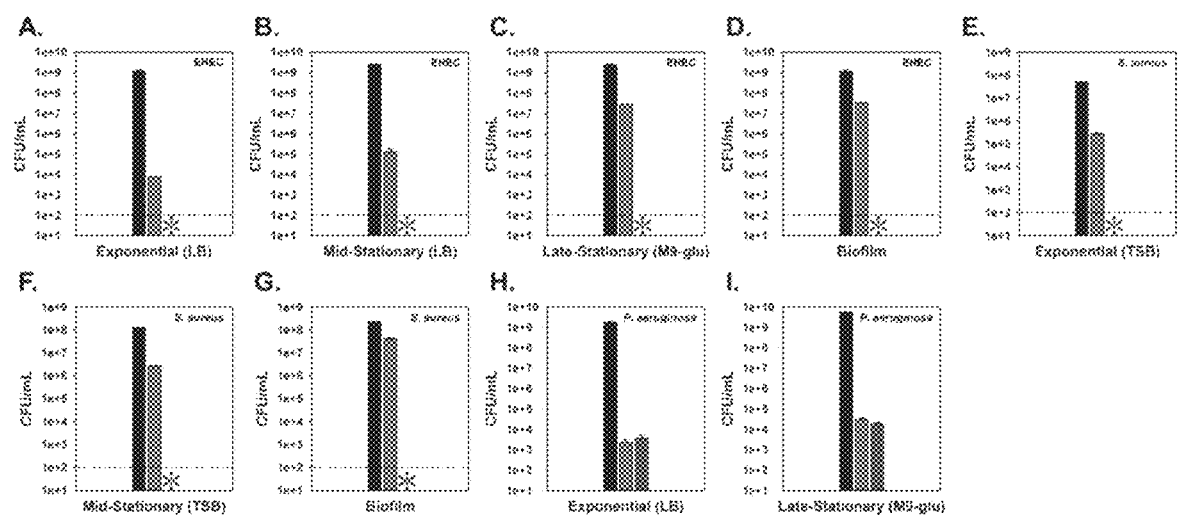

FIG. 3: MMC eradicates pathogens in suspension and in biofilms. Cell viability of EHEC exponential (A) and mid-stationary phase (B) cultures in buffered LB, late-stationary phase cultures in M9-glucose (C), and biofilm cultures in M9-glucose (D). Cell viability of S. aureus exponential (E) and mid-stationary phase cultures in tryptic soy broth (TSB) (F), and biofilm cultures in modified M9-glucose (G). Cell viability of P. aeruginosa PA14 exponential phase cultures in buffered LB (H) and late-stationary phase cultures in M9-glucose (I). Cell viability is shown before (black/left bar for each panel) and after treatment with ciprofloxacin (green/bar to immediate right of "before treatment" bar) and MMC (red/right bar, except where * represents eradication beyond the limit of detection. Means±s.d. are shown throughout (n≥2).

Figure 4:
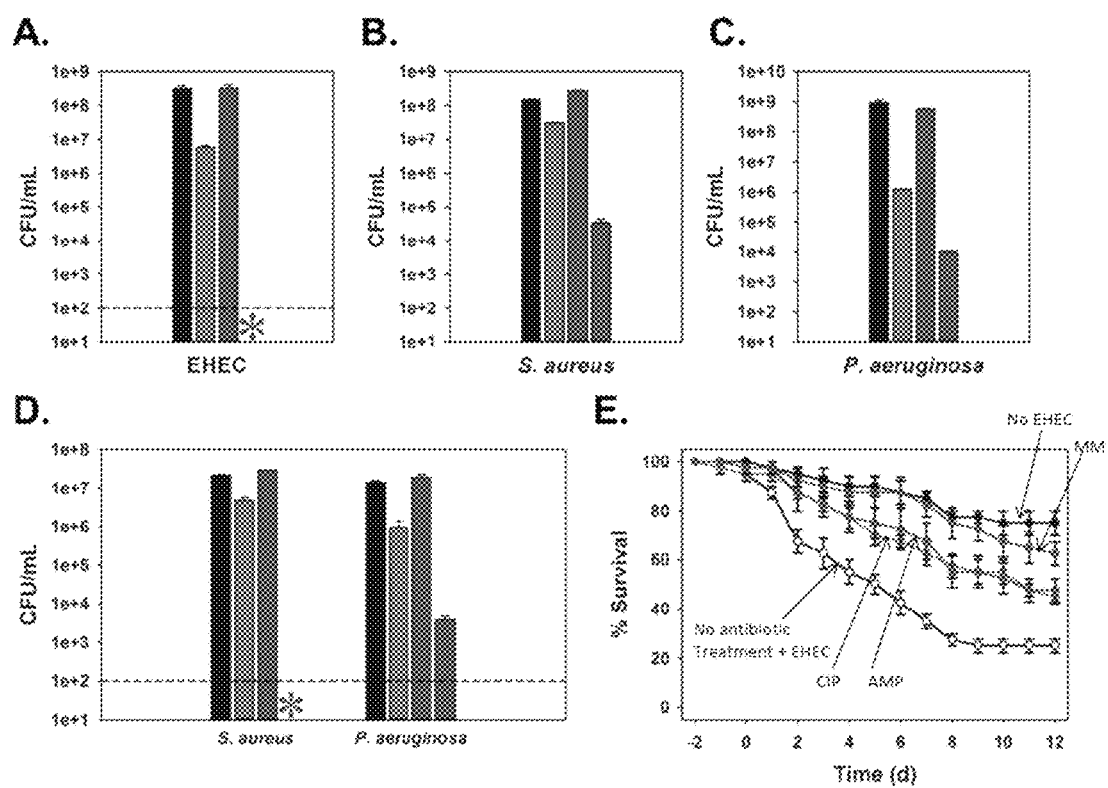

FIG. 4: MMC eradicates pathogens in a clinically relevant wound model. Cell viability of EHEC (A), S. aureus (B), and P. aeruginosa PAO1 (C) mono-cultures and S. aureus and P. aeruginosa PAO1 co-cultures (D) in an in vitro wound model. Cell viability is shown before (black/left bar in each panel) and after treatment with ciprofloxacin (green/second bar from left in each panel), ampicillin (blue/third bar from left in each panel), and MMC (red/right bar, except where * represents eradication beyond the limit of detection by MMC. (E) Graph shows: survival of C. elegans after infection with EHEC (days −2 to 0), exposure to ciprofloxacin (green), ampicillin (blue), MMC (red), or no treatment (white). As a negative control, C. elegans was grown on OP50 without antibiotic treatment and no EHEC (black). Means±s.d. are shown throughout (n≥2).

Figure 5:
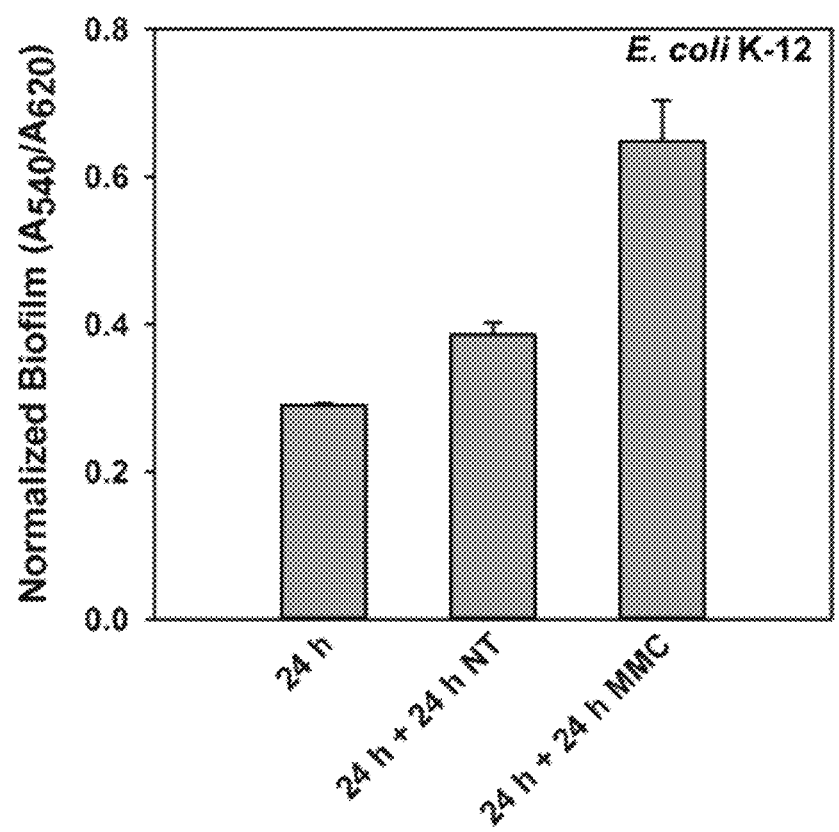

FIG. 5: MMC does not cause biofilm dispersal. Biofilm formation for E. coli K-12 BW25113 wild-type cultures after 24 h of static growth and after an additional 24 h of static growth with no treatment (NT) or with MMC treatment (MMC) at 30° C. in M9-glucose. Means±s.d. are shown throughout (n≥2).

Figure 6:
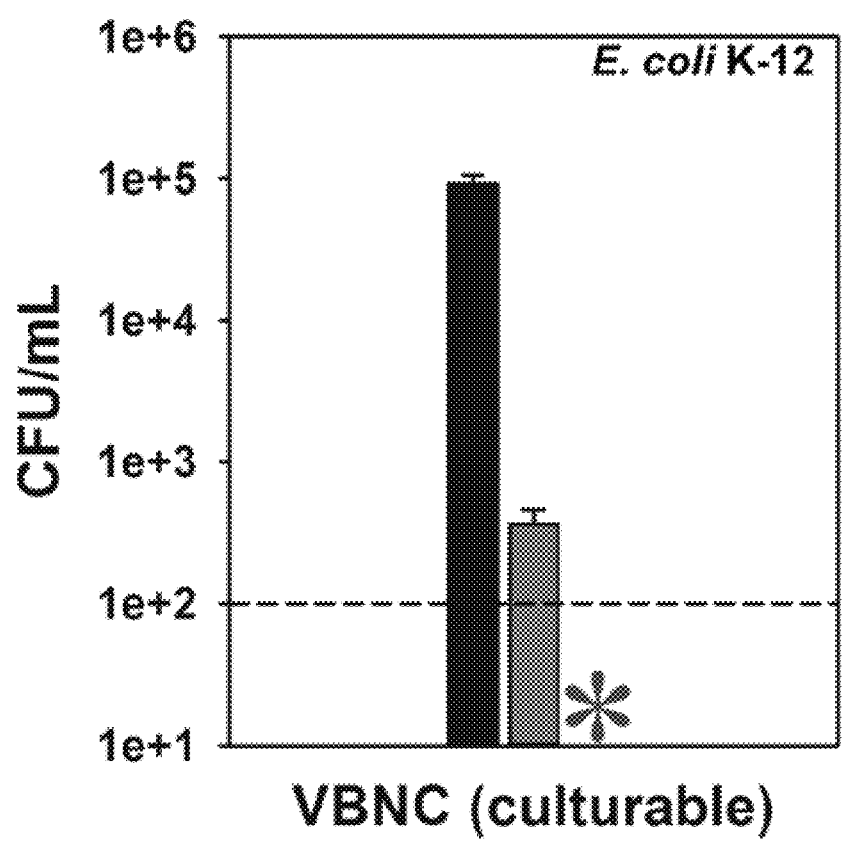

FIG. 6: MMC eradicates the culturable population in VBNC cultures. Cell viability of the culturable population of E. coli K-12 BW25113 VBNC cultures. Cell viability is shown before (black/left bar) and after treatment with ciprofloxacin (green/bar left of *) and MMC (red). * represents eradication beyond the limit of detection. Means±s.d. are shown throughout (n≥2).

Figure 7:
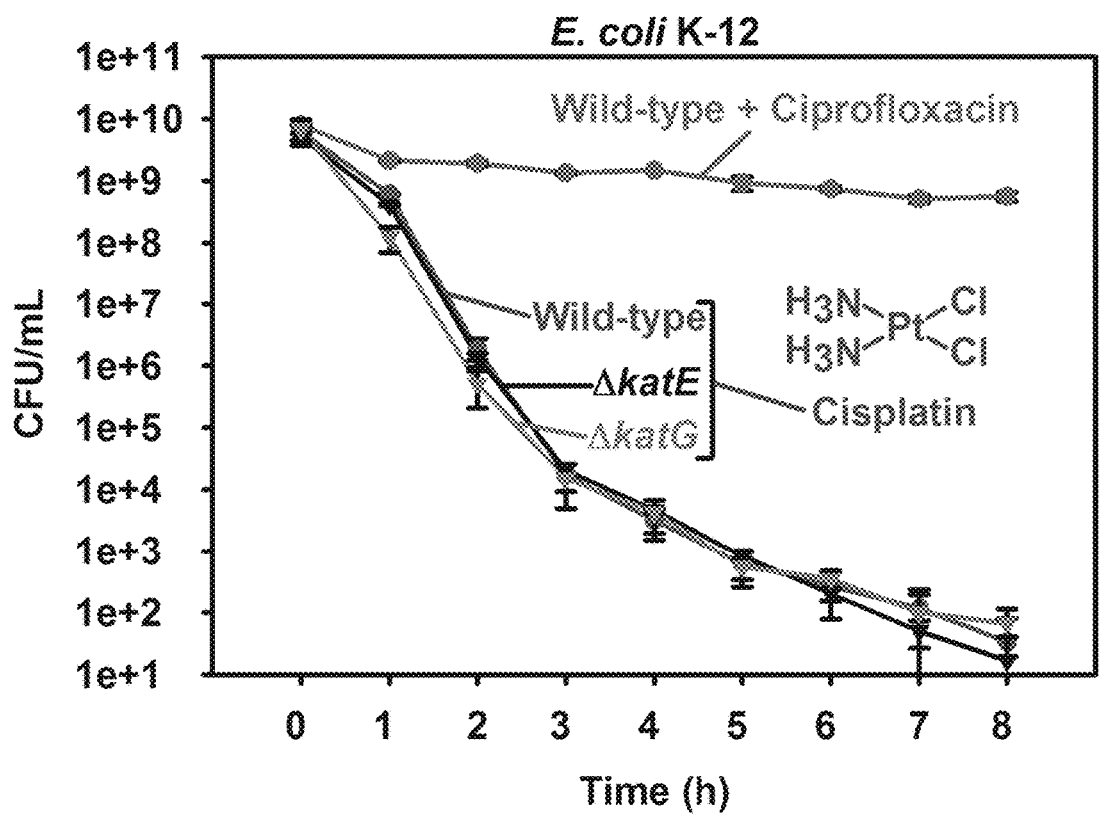

FIG. 7: Cisplatin eradicates late stationary-phase E. coli K-12 cells. Time course dependent killing of late-stationary phase (16 h of growth) cells of wild-type E. coli K-12 in buffered LB by ciprofloxacin (5 μg/mL, 100×MIC, green line) and cisplatin (500 μg/mL, 5× MIC, red line). Killing with cisplatin (500 μg/mL) for two isogenic catalase mutants ΔkatE (black line) and ΔkatG (blue line) is also indicated. The structure of cisplatin is shown as an inset.

Figure 8:
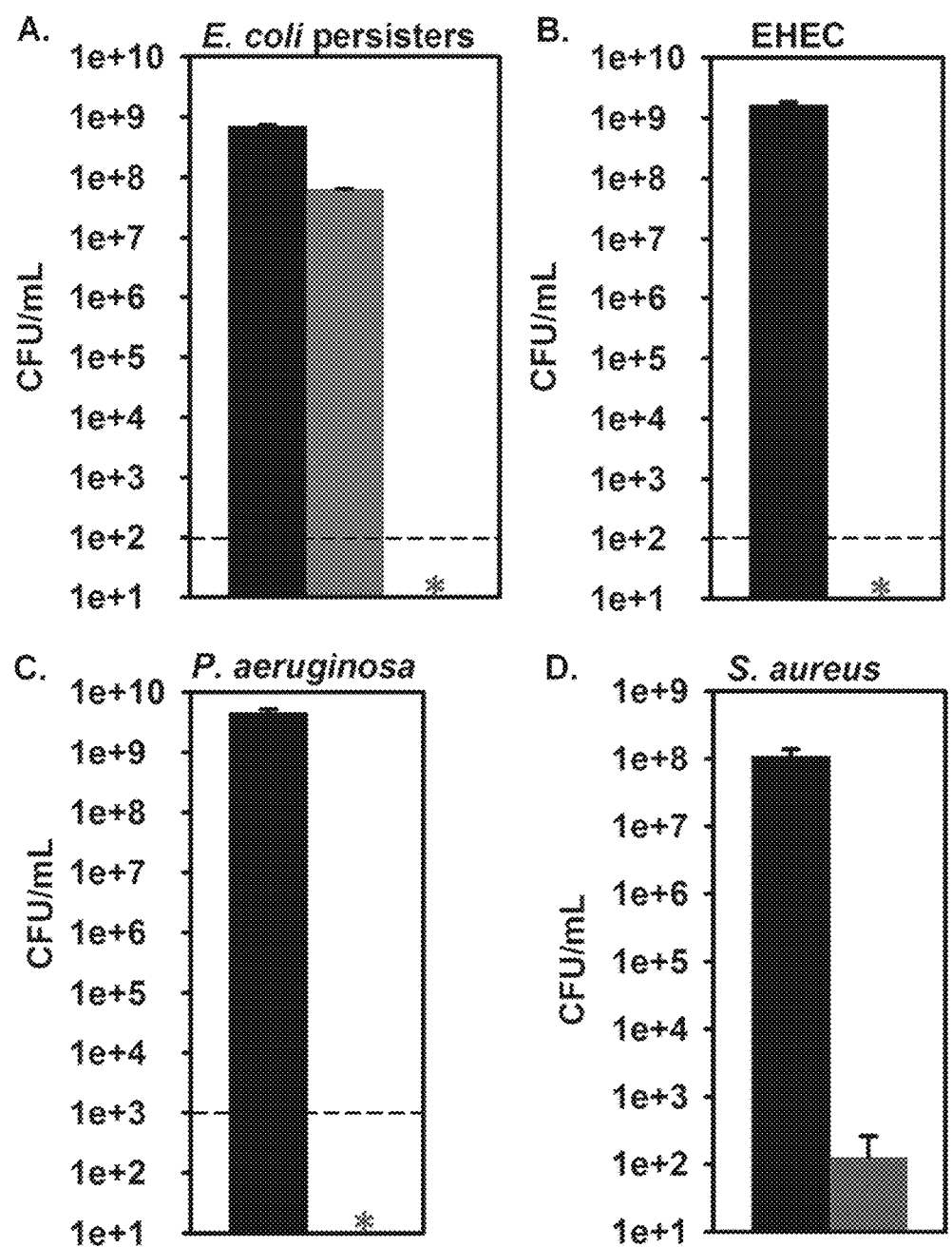

FIG. 8: Cisplatin eradicates metabolically dormant persister cells and has broad spectrum activity against diverse bacterial pathogens. (A) Cell viability of rifampicin (30 min pretreatment with 100 μg/mL)-induced persister cells of E. coli K-12 in buffered LB after treatment with ciprofloxacin (5 μg/mL, 100×MIC) and cisplatin (500 μg/mL, 5×MIC). (B) Stationary-phase cells of EHEC in buffered LB after treatment with cisplatin (500 μg/mL, 5× MIC). (C) Stationary-phase cells of P. aeruginosa in M9-glucose (0.4%) after treatment with cisplatin (250 μg/mL, 5×MIC). (D) Stationary-phase cells of S. aureus in TSB medium after treatment with cisplatin (500 μg/mL, 1.7×MIC). Cell viability is shown before (black bar—left most bar in each of A, B, C and D) and after 3 h treatment (green bar for ciprofloxacin (bar to immediate right of black bar in A) and red bar (bar to immediate right of black bar in D) or red asterisk for cisplatin). *Represents eradication of cells beyond the limit of detection (100 cells/mL).

Figure 9:
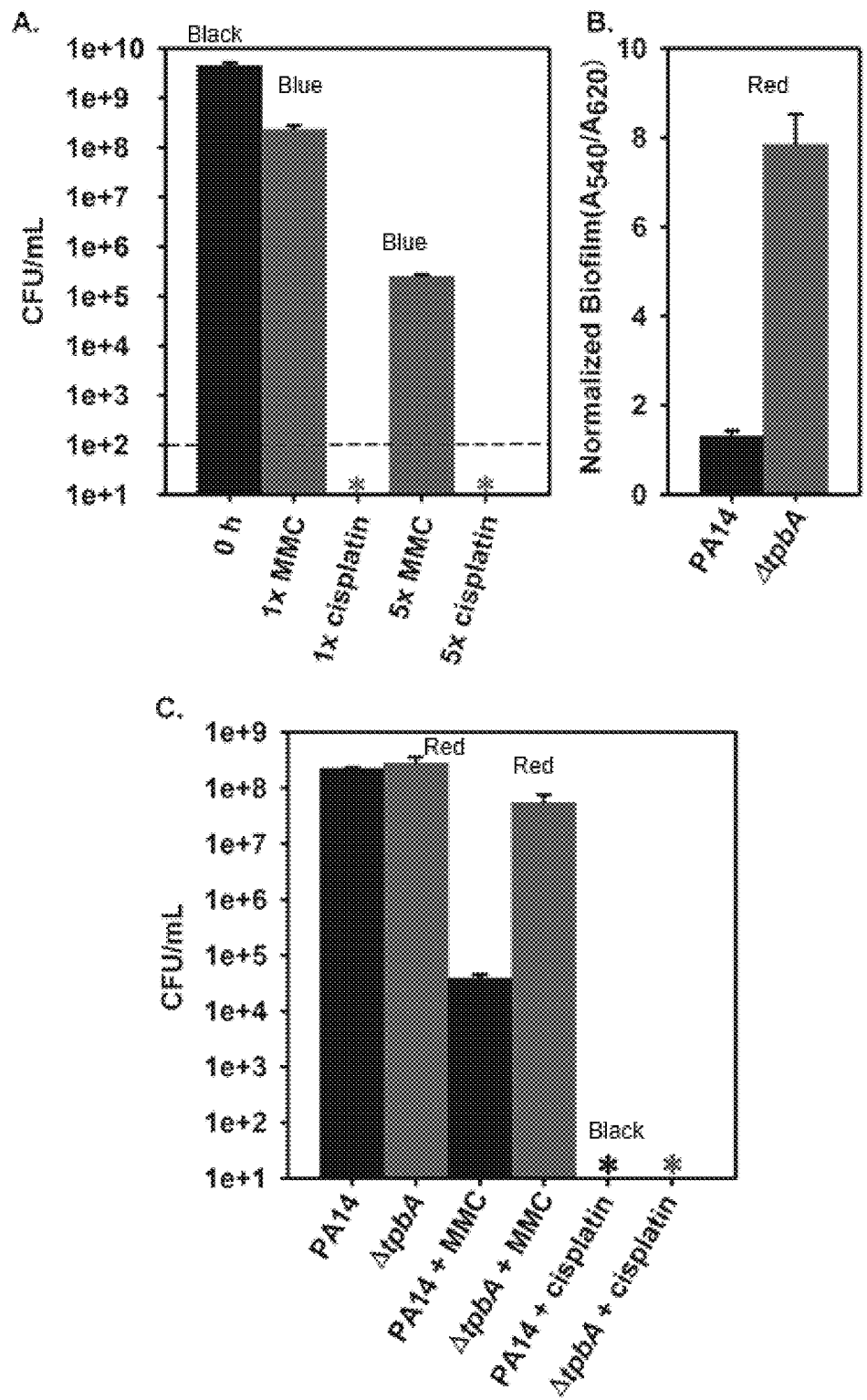

FIG. 9: Cisplatin is more effective than mitomycin C (MMC) in killing P. aeruginosa planktonic and biofilm persister cells. (A) Cell viability of P. aeruginosa PA14 planktonic (stationary-phase) cells before (black bar) and after treatment for 3 h with 1× and 5× MIC of MMC (2 μg/mL and 10 μg/mL, respectively; blue bars (1×MMC and 5×MMC in 9A) and 1× and 5× cisplatin (50 μg/mL and 250 μg/mL, respectively; red asterisks). (B) Comparison of biofilm production between wild-type P. aeruginosa PA14 (black bar/left most bar in 9B) and its isogenic mutant strain ΔtpbA (red bar/right bar in 9B) in M9-glucose (0.4%) medium. (C) Cell viability of biofilm cells of P. aeruginosa PA14 (black bar) and ΔtpbA (red bar) before and after treatment for 3 h with 10 μg/mL of MMC (5×MIC) or 250 μg/mL of cisplatin (5× MIC). *Represents eradication of cells beyond the limit of detection (100 cells/mL).

Figure 10:
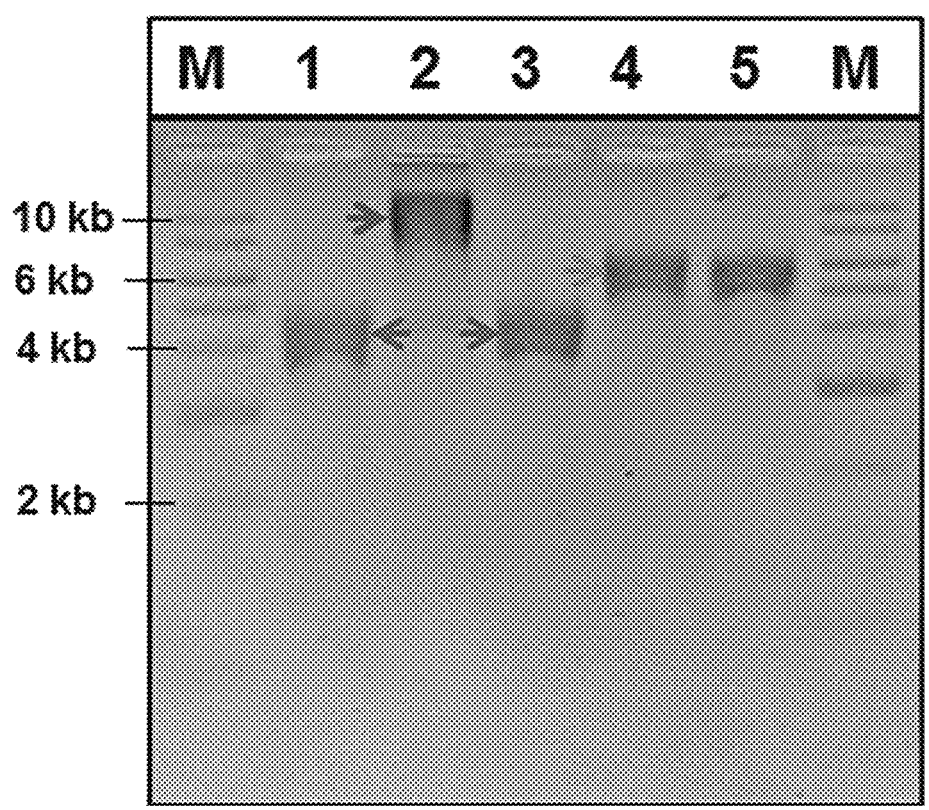

FIG. 10: Cisplatin crosslinks intra-strand DNA and MMC crosslinks inter-strand DNA in vitro. Denaturing agarose gel electrophoresis of cisplatin (lane 4, 1.5 h treatment; lane 5, 3.5 h treatment) and MMC (lane 2, 1 h treatment) crosslinked pCA24N DNA. Red arrow (pointing right at lane 2) indicates migration of MMC-crosslinked DNA as MMC crosslinks different strands of DNA, blue arrows (pointing left at lane 1 and right at lane 3) indicate migration as single-stranded DNA as reagent control for MMC (lane 1) and NaClO₄ as the solvent control for cisplatin (lane 3) that did not crosslink DNA, and green arrow (pointing right at lane 4) indicates migration as crosslinked single-stranded DNA as it migrated slower than non-crosslinked, single-stranded DNA but faster than MMC crosslinked double-stranded DNA. 'M' indicates 1 kb DNA ladder (New England Biolab, Ipswich, Mass., USA).

DETAILED DESCRIPTION

The present disclosure provides methods for reducing bacterial persister cells and/or dormant viable but non-culturable (VBNC) cells. The persister and/or VBNC cells may be present in population that comprises or consists of such cells. The method comprises administering an effective amount of the anti-cancer drug mitomycin C (MMC), or cisplatin, or derivatives of MMC and cisplatin, and combinations thereof, wherein the bacterial persister cells and/or the VBNC cells in the population are reduced or eradicated.

Unlike the majority of antibiotics which rely on cell activity to damage cells (e.g., fluoroquinolones inhibit DNA gyrase to cause damage from supercoiling during replication), MMC and cisplatin directly damage cells by creating DNA crosslinks. This disclosure provides a demonstration that MMC, an FDA approved drug, and cisplatin, also an FDA approved drug, are effective in killing a broad-range of bacterial persister cells, including but not necessarily limited to those formed in biofilms and wounds.

Cisplatin (cis-diamminodichloroplatinum(II) (FIG. 7) has been used to treat testicular, ovarian, bladder and head and neck cancers. Like MMC, cisplatin crosslinks DNA but the crosslinks occur primarily on the same strand of DNA with intrastrand crosslinks between purines at adjacent guanines (54-65%), at AG sequences (17-19%), and at GNG sequences where N can be any nucleotide (<8%) (Eastman, A. *The formation, isolation and characterization of DNA adducts produced by anticancer platinum complexes*. Pharmacol. Ther. 34, 155-166, (1987)). In this disclosure it is demonstrated that cisplatin-induced DNA damage can, in certain embodiments, eradicate all bacterial cells in a bacteria population, including persisters, and that cisplatin is more effective at this than MMC. Thus, the disclosure comprises use of MMC, or cisplatin, or combinations of these two agents or their derivatives, to combat persister cells.

"Persister cells" as used herein means pathogenic bacteria that neither grow nor die in the presence of microbicidal antibiotics (with the exception of MMC and cisplatin, as described herein). In embodiments, persister cells contribute to the recalcitrance of clinical infections in cystic fibrosis, tuberculosis, and wounds. In certain embodiments the disclosure includes reducing the number of persister cells in a population of persister cells, or eradicating an entire population of persister cells. The population of persister cells can be present in an infection, or in a liquid culture, or on an inanimate surface. In non-limiting examples the surface can be a non-porous surface, a surface in a hospital, or a surface that is used for food processing or preparation. Additional surfaces are described herein.

In embodiments, the persister cells and/or VBNC cells that are reduced or eradicated according to the present disclosure are responsible for or are positively correlated with the presence of recalcitrant infections, such as chronic recalcitrant infections. For example, as is well known in the art, when the functioning of an individual's immune system is less than optimal, an infection can become chronic. Known examples of chronic infection occur in a variety of individuals, such as those who are immunocompromised because of immunosuppressive drug courses, co-infection with viruses, or individuals who have an infection that forms a biofilm. As is also well known in the art, biofilms impede access of immune cells and immunological signaling molecules to bacteria, and thus limit the effectiveness of even normally functioning immune systems. Further, biofilms are known to form in a variety of wounds inside the body, as well as on surfaces of indwelling medical devices. In certain instances, such infections and biofilms can be populated by drug-resistant bacteria present on the devices, and in the tissue that comes into contact with them. However, in many instances chronic and recalcitrant infections arise because comparatively slow-growing bacteria develop into drug-tolerant persister cells that are difficult to eradicate with currently used antibiotics, and this can occur with or without the presence of an implanted device. Thus, upon cessation of a course of antibiotics and the subsequent decrease in its concentration, persister cells can exploit an opportunity to grow and repopulate the infection and/or biofilm. The approaches of the present disclosure are particularly suited for reducing the number of and/or eradicating such cells.

In certain embodiments, performing a method of this disclosure results in a reduction of the persister cells and/or the VBNC cells, wherein the reduction is greater than a reference. The reference can comprise any suitable control, value or measurement of the killing of persister cells, such as a standardized curve, a titration, the area under a curve, or a comparison to the capability of another antimicrobial compound to kill the persister cells and/or the VBNC cells. In an embodiment, the reference comprises a value obtained from measuring the amount of persister cells and/or VBNC cells of the same bacterial species that are killed using an antibiotic that is not MMC, or cisplatin, or a combination thereof, depending on the circumstances and as will be readily apparent to those skilled in the art, given the benefit of the present disclosure. In embodiments, the amount of the reference antibiotic used to compare to MMC or cisplatin is matched, i.e., an amount of the reference antibiotic that kills non-persistent cells at the same minimum inhibitory concentration (MIC) of MMC, or cisplatin, respectively.

The present disclosure can comprise use of a composition comprising MMC/cisplatin, or derivatives or combinations thereof, as the only antimicrobial agent(s) in the composition, or the composition can also comprise other antimicrobial agents. In embodiments, the disclosure encompasses using MMC/cisplatin in the same composition as at least one other antimicrobial compound, or in concurrent or sequential, distinct administrations wherein MMC and/or cisplatin is administered separately from at least one other antimicrobial compound, examples of which include but are not limited to any known antimicrobial compound other that MMC and cisplatin, and/or compounds that interfere with, for example, bacterial quorum sensing. In various embodiments, the MMC and/or cisplatin compounds can be used with antibiotics that are members of classes such as aminoglycosides, beta lactams (with or without beta lactamase inhibitor such as clavulanic acid), macrolides, glycopeptides, polypeptides, cephalosporins, lincosamides, ketolides, rifampicin, polyketides, carbapenem, pleuromutilin, quinolones, streptogranins, oxazolidinones, lipopeptides, etc.

In another aspect the disclosure includes an article of manufacture comprising packaging material and one or both of cisplatin and MMC, provided in separate or in a single pharmaceutical formulation in the packaging material, wherein the pharmaceutical composition is effective for reducing and/or eradicating persister and or VBNCs, and wherein the packaging material optionally comprises a label or other printed material which provides an indication that the agents can be used for killing bacterial populations as described herein.

As stated above, the disclosure includes use of a composition comprising MMC, cisplatin, derivatives and combinations thereof, as the only antimicrobial agent(s) in the composition, but can include other antimicrobial agents as well. But in certain embodiments, the compositions comprising MMC/cisplatin are not administered in combination with any polypeptide or peptide antimicrobial agent(s), non-limiting examples of which include any polypeptide or fragment thereof encoded by the bacterial DinQ gene, or any DNA or RNA polynucleotide that is part of or encoded by the DinQ gene. In embodiments, the MMC/cisplatin is not administered in combination with any anti-cancer agent that is not MMC or cisplatin. In embodiments, the MMC or cisplatin is not administered in combination with rifalazil. In embodiments, the MMC or cisplatin is not administered in combination with a thioesterification agent. In embodiments, the MMC or cisplatin is not administered in combination with an α-adrenergic antagonist, an anthelmintic agent, an antifungal agent, an antimalarial agent, an antineoplastic agent, an antipsychotic agent, an antioxidant, a vasodilator, or a vitamin. In embodiments, the MMC or cisplatin is not administered in combination with a drug that is metabolized by CYP450. In embodiments, the MMC or cisplatin is not administered in combination with a non-pathogenic and/or attenuated bacterium. In embodiments, the MMC or cisplatin is not administered in combination with a substituted benzazole derivative. In embodiments, the MMC or cisplatin is not administered in combination with calreticulin protein, or an ERP57. Each of the foregoing exclusions includes the situation where the MMC and/or cisplatin would be administered with the excluded compound(s) concurrently or sequentially, and includes MMC and or cisplatin derivatives as an alternative to MMC and cisplatin.

MMC and cisplatin derivatives suitable for use with the present disclosure are known in the art. It is expected that any MMC and cisplatin derivatives could be used, provided they also function to cross-link bacterial DNA. Thus, all microorganisms susceptible to the anti-bacterial mechanism of MMC and cisplatin described herein may be suitable for use in methods of this disclosure. In embodiments, the MMC/cisplatin derivatives used in the present disclosure have not previously been described for use as anti-microbial compounds, and/or have not been previously described or demonstrated to be useful for eradicating persister pathogenic bacteria. In certain embodiments, the MMC derivatives are mitomycin alcohol, or etoposide, or MMC prodrugs, or MMC coupled via a tri- or tetrapeptide spacer onto poly-[5N-(2-hydroxyethyl)-L-glutamine] (PHEG), MMC derivatives with aromatic moieties such as 1a-N-Benzylmitomycin C, or MMC 7-N-phenyl derivatives. In certain embodiments, the cisplatin derivatives are [PtCl$_2$(NH$_3$)(1-methyl-7-azaindole] described in J. Med. Chem. 2015, 58, 847-859, as well as the approved anti-cancer derivatives carboplatin, oxaliplatin, and nedaplatin.

Various methods known to those skilled in the art may be used to administer compositions comprising MMC/cisplatin or derivatives thereof for the purpose of reducing or eradicating populations of persister cells and/or VBNC cells, including such populations when they are present in an infection in an individual. These methods include but are not necessarily limited to intradermal, transdermal, intravenous, topical, intramuscular, intraperitoneal, intravenous, subcutaneous, oral, and intranasal routes. In certain aspects the disclosure includes providing the compounds in the form of creams, aqueous solutions, suspensions or dispersions, oils, balms, foams, lotions, gels, cream gels, hydrogels, liniments, serums, films, ointments, sprays or aerosols, other forms of coating, or any multiple emulsions, slurries or tinctures. The compositions may be embedded in materials, such as a medical device or other implement used in treating or manipulating a body, organ, tissue or biological fluid. The compositions can also include liposomes, microsomes, nanoparticles, and any other suitable vehicle for delivering the compounds such that they reduce or eradicate persister cells where present. Further, it will be recognized by those of skill in the art that the form and character of the particular dosing regimen employed in the method of this disclosure will be dictated by the route of administration and other well-known variables, such as the age, sex, health and size of the individual, the type and severity of bacterial infection, or risk of bacterial infection, and other factors that will be apparent to the skilled artisan given the benefit of the present disclosure. MMC dosages are expected to be administered at concentrations between 0.5-2.0 μg/mL (20-80 mg/m$^2$) and topical dosages have been safely applied at concentrations up to 400 μg/mL. Cisplatin dosages are expected to be administered at concentrations of 50 to 100 μg/mL. To improve the time in blood circulation, MMC and/or cisplatin may be combined with nano-formulations comprised of microemulsions, carbon nanoparticles, true nano-spheres, or polyanionic PEG-polyglutamate co-polymers. In certain embodiments the disclosure comprises contacting a population of bacteria that comprises or consists of persister cells and/or VBNCs, and reducing and or eradicating the population by contacting the population with MMC, cisplatin, derivatives thereof, and/or combinations thereof.

In embodiments, the disclosure can exclude administering MMC or cisplatin to any individual diagnosed with or suspected of having cancer, and/or any individual to whom MMC or cisplatin has been previously administered, or to whom MMC or cisplatin would be a candidate for administration for any purpose other than a known or suspected bacterial infection comprising persister or VBNC cells.

In certain embodiments, the method of the disclosure results in eradication of a bacterial population comprising the bacterial persister cells and/or VBNC cells from an infection, such as from an infection of an organ, tissue, skin, or biological fluid from an individual, or from the surface of an inanimate object, including but not necessarily limited to medical devices, such as implantable or implanted medical devices, and/or any medical device that may stay in contact with the skin or be fully or partially present within the body of an individual for a period of time during which the surface of the device may be susceptible to biofilm formation. In certain aspects compositions comprising the MMC and/or cisplatin and/or derivatives thereof, In embodiments, the persister cells and/or VBNC cells are resistant to one or more antibiotics other than MMC, including but not necessarily limited to the list of antibiotics disclosed above.

In embodiments, the method of this disclosure is used to reduce or eradicate persister cells and/or VBNC cells that are present in anaerobic conditions.

In embodiments, the method of this disclosure is used to reduce or eradicate pathogenic Gram-negative bacteria, or pathogenic Gram-positive bacteria, or a combination thereof.

In embodiments, the method of this disclosure is used to reduce or eradicate pathogenic persister and/or VBNC cells that are mid-stationary phase or late-stationary phase cells.

In certain embodiments, the disclosure is used to reduce or eradicate persister cells and/or VBNC cells that are *E. coli, V. cholerae, P. aeruginosa, B. burgdorferi, Streptococcus* spp., *S. typhimurium, S. aureus, E. faecalis, A. baumannii, A. iwoffii, S. marcescens, P. mirabilis, K. pneumoniae, A. calcoaceticus, S. mutans, P. gingivalis, H. influenza, H. pylori, N. meningitides, N. gonorrhea, M kansasii, B. anthracis, P. acnes, C. tetani, C. trachomatis, L. pneumophila, Y. pestis, B. abortus, F. tularensis, V. harveyi*, and combinations thereof.

In certain embodiments, the present disclosure is used to reduce or eradicate persister cells and/or VBNC cells that are present in a wound of an individual.

In embodiments, the method comprises administering a composition comprising an effective amount of MMC/cisplatin or a derivative(s) thereof to an individual who is known to be in need of reducing or eradicating an infection, including an infection comprising persister cells and/or VBNC cells. In embodiments, the may further comprise subsequently testing a biological sample from the individual to verify the reduction and/or eradication. In non-limiting embodiments, the individual has been diagnosed with cystic fibrosis, tuberculosis, or has a wound that comprises a recalcitrant infection.

In certain embodiments, the present disclosure is used to reduce or eradicate persister cells and/or VBNC cells in an infection in an individual who has been diagnosed with a bacterial infection and has been treated with at least one antibiotic other than MMC or cisplatin, and wherein the diagnosed bacterial infection was not cleared by the previous treatment. In embodiments, the individual was previously treated with rifampicin.

In certain embodiments, the present disclosure is used to reduce or eradicate persister cells and/or VBNC cells that are present in a biofilm. In a non-limiting example, the bacterial persister cells and/or VBNC cells are reduced or eradicated from a biofilm, but the biofilm is not dispersed.

In certain embodiments the disclosure includes reducing or eradicating persister cells that may be present on an inanimate surface, such as an implanted medical device, or other surface outside a body.

In certain embodiments, the disclosure entails reducing or eradicating persister cells and/or VBNC cells by using MMC or cisplatin or their derivatives at a concentration such that DNA in the persister cells and/or VBNC cells is cross-linked, such as cross-linked double strands of the bacterial genomic DNA, and wherein the cross-linking is adequate to be lethal to the cells.

The following Example are intended to illustrate but not limit the disclosure.

Example 1

In arriving at the current disclosure, and described above, we found that MMC is effective against persister cells in a broad range of bacteria including commensal *Escherichia coli* K-12 as well as pathogenic strains of *E. coli, Staphylococcus aureus* (frequently found in wounds), and *Pseudomonas aeruginosa* (also frequently found in wounds). We also demonstrated that MMC eradicates bacteria in biofilms, communities of notoriously difficult to treat cells present in a majority of infections. Furthermore, we verified that MMC kills persister cells by crosslinking DNA, and we demonstrated the efficacy of MMC in an animal model and in a wound model. Therefore, MMC has broad-spectrum activity against growing, non-growing, and persister cells, and should be used for the treatment of recalcitrant infections.

MMC activity is decreased at high pH; hence, we buffered the medium to avoid high pH fluctuations and to match the physiological resting pH of ~7.4 and exercising pH of ~7.1 and ~6.4. We compared MMC with ciprofloxacin, a fluoroquinolone that inhibits DNA replication and kills both growing and non-growing cells but not persister cells and which is commonly used in persister studies. We initially evaluated MMC with *E. coli* K-12 and found, compared to ciprofloxacin, that MMC was 2,300-fold more effective against exponentially-growing cells (FIG. 1A) and 150,000-fold more effective against mid-stationary-phase cells in buffered lysogeny broth (LB) medium (FIG. 1B). As evidence of the ability of MMC to kill persister cells, we found that treatment of a late-stationary phase culture with MMC does not show the bi-phasic death curve that is characteristic of a persister population (FIG. 1C). We then utilized a rifampicin pretreatment which we previously demonstrated to induce high levels of persistence (~10-100%) and found that MMC was highly effective against rifampicin-induced persister cells, in stark contrast to ciprofloxacin (FIG. 1D). Therefore, MMC kills non-persister cells and dormant persister cells.

The previous assays were performed in planktonic cultures grown in rich medium; however, these growth conditions are a poor representation of ecological bacterial growth. Thus, we investigated MMC activity against cultures grown in minimal medium, in biofilms, and in anaerobic cultures. Exponential-phase cultures in M9-glucose were similarly susceptible to MMC and ciprofloxacin (FIG. 1E); however, during late-stationary phase in M9-glucose, we found that while the population was highly persistent against ciprofloxacin (10±1%) and the aminoglycoside gentamicin (44±5%), MMC eradicated cells (FIG. 1F). Biofilms more accurately model clinical bacteria growth with a high population of persisters, and we found that MMC was effective against biofilms in M9-glucose, killing 100,000-fold more cells than ciprofloxacin and nearly eliminating cells after 24 h of treatment (FIG. 1G). Additionally, MMC did not cause biofilm dispersal, confirming that efficacy against biofilms was in fact due to eradication of cells (FIG. 5). Bacterial infections have a propensity to exist under anaerobic conditions, and we found that MMC eradicated anaerobic, late-stationary phase cells in rich medium beyond the limit of detection, in comparison to 0.44±0.08% survival against ciprofloxacin treatment (FIG. 1H). Furthermore, anaerobic biofilm cultures in M9-glucose were 2,500-fold more susceptible to MMC than ciprofloxacin (FIG. 1I).

Numerous species of bacteria enter the dormant viable but non-culturable (VBNC) state as a survival response to environmental stresses, and these cells do not resuscitate and become culturable unless exposed to suitable stimuli. VBNC cells exhibit high antibiotic tolerance, similarly to persisters, and pose a risk to human health because they can avoid detection in goods, leading to infection. Hence, we generated VBNC cultures by starving cells in saline solution for 36 days until there were ~1,000-fold more VBNC cells than culturable cells. Respiratory activity is a commonly used criterion for viability, so RedoxSensor Green, a fluorescent dye for detection of actively respiring cells, was used to enumerate the VBNC population. Upon antibiotic treatment of these cultures, we found that MMC was 7-fold more effective at killing VBNC cells than ciprofloxacin (FIG. 1J), while also eradicating the culturable population (FIG. 6), unlike ciprofloxacin (0.40±0.05% survival). Therefore, we have demonstrated that MMC is highly effective against metabolically dormant cells in both the persister and VBNC states.

Figure 2:
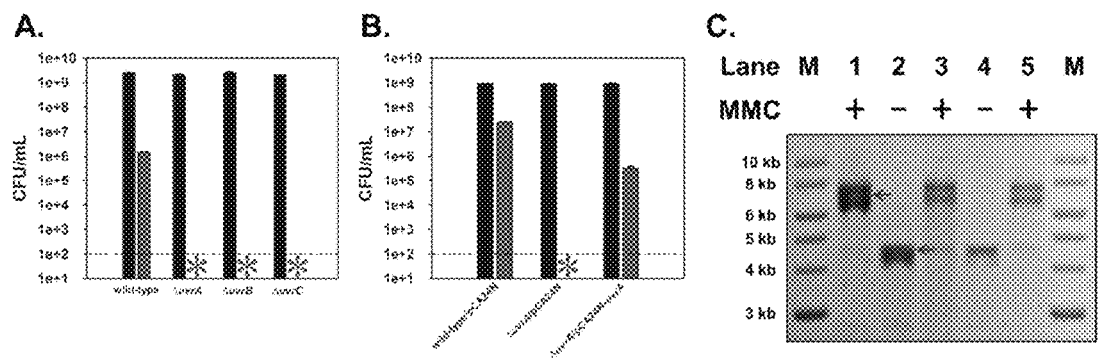
FIG. 2: MMC crosslinks DNA in *E. coli* K-12 persister cells. (A) Cell viability of *E. coli* K-12 wild-type, ΔuvrA, ΔuvrB, and ΔuvrC mid-stationary phase cultures in buffered LB treated for 30 min with MMC. (B) Cell viability of *E.* coli K-12/pCA24N, ΔuvrA/pCA24N, and ΔuvrA/pCA24N-uvrA exponential phase cultures in buffered LB treated for 1 h with MMC. Cell viability is shown before (black/left bar for each culture) and after treatment with MMC (red/right bar for each culture except where * represents eradication beyond the limit of detection by MMC. The limit of detection was determined by analyzing the number of viable cells remaining by culturing bacteria on agar plates. Means±s.d. are shown for A and B (n≥2). (C) Denaturing gel electrophoresis for pDNA (4,518 nt) from E. coli K-12/pCA24N non-persisters (lanes 2 and 3) and rifampicin-induced persisters (lanes 4 and 5) before (lanes 2 and 4) and after (lanes 3 and 5) MMC treatment. Lane 1 is a positive control with in vitro crosslinked pDNA. "M" indicates the DNA ladder, the red arrow (pointing left at lane 1) indicates migration as double-stranded (i.e., cross-linked) DNA, and the blue arrow (pointing left at lane 2) indicates migration as single-stranded DNA.

To verify that MMC kills bacteria via DNA crosslinks, we investigated MMC activity against single-gene deletion mutants lacking uvrA, uvrB, and uvrC. The UvrABC complex is part of the bacterial SOS response in *E. coli* to repair DNA crosslinks, and contributes to MMC tolerance. We found that the ΔuvrA, ΔuvrB, and ΔuvrC mutants were much more sensitive to MMC than the wild-type strain, and were rapidly eradicated (beyond the limit of detection) within less than 30 min of treatment (FIG. 2A). Additionally, we were able to complement the high sensitivity to MMC of a ΔuvrA mutant with production of UvrA via plasmid (FIG. 2B). These results confirm that DNA crosslinking is the basis for MMC bactericidal activity in actively-growing cells.

However, persister cells are dormant, thus having a different metabolic state than non-persisters. Therefore, we sought to verify that MMC was in fact forming DNA crosslinks within persisters, rather than killing persisters through an unknown mechanism. Genomic DNA (gDNA) was isolated from both exponential phase cells (i.e., non-persisters) and rifampicin-induced persistersbefore and after MMC treatment. We hypothesized that crosslinks within DNA should inhibit amplification via quantitative PCR (qPCR). qPCR was performed with primers designed to amplify a 234 nt region of rrsG and a 302 nt region of murB, containing 18 and 10 potential MMC crosslinking sites, respectively. As a positive control, qPCR was performed on gDNA crosslinked by MMC in vitro, verifying that DNA crosslinking inhibited amplification dramatically (rrsG: −1,456±1 fold and murB: −1,621±28 fold). Our in vivo results revealed the presence of gDNA crosslinks based on reduced quantities of PCR-amplifiable DNA after MMC treatment for non-persisters (rrsG: −5.95±0.20 fold and murB: −5.13±0.14 fold) and persisters (rrsG: −5.01±0.51 fold and murB: −5.99±0.50 fold) (Table 3).

Crosslinked DNA runs differently from non-crosslinked DNA after denaturation because the crosslinks covalently bind the two strands, preventing separation. As confirmation of DNA crosslinking within persister cells found with qPCR, we isolated plasmid DNA (pDNA) from both exponential-phase cells (i.e., non-persisters) and rifampicin-induced persisters before and after MMC treatment and performed agarose gel electrophoresis under denaturing conditions to allow uncrosslinked DNA to migrate as single strands. Under denaturing conditions, pDNA samples from cells without MMC treatment migrated as single-stranded DNA, while samples for both non-persisters and persisters treated with MMC showed a high percentage of crosslinking, based on migration as double-stranded DNA (FIG. 2C). DNA treated in vitro with MMC migrated in the expected manner as double-stranded DNA. Therefore, we have demonstrated by two independent means that MMC does in fact crosslink the DNA of persister cells.

Clinical application of MMC is dependent on efficacy against pathogenic bacteria. Therefore, we tested the ability of MMC to kill *E. coli* O157:H7 (EHEC) a common pathogenic strain of Gram-negative *E. coli*. MMC was substantially more effective than ciprofloxacin against EHEC, eradicating both exponential (FIG. 3A) and mid-stationary phase cells (FIG. 3B) in rich medium beyond the limit of detection. Additionally, MMC eradicated late-stationary phase EHEC cells in M9-glucose beyond the limit of detection, while 1.2±0.1% of cells survived against ciprofloxacin (FIG. 3C). Biofilm cultures of EHEC were also eradicated (beyond the limit of detection) after 24 h of MMC treatment, in comparison to 3±1% of cells surviving ciprofloxacin (FIG. 3D).

MMC was also tested against Gram-positive *S. aureus* (methicillin sensitive) and Gram-negative *P. aeruginosa*, two other common species of human pathogens. Against planktonic cultures of *S. aureus* grown in rich medium, MMC was highly effective, eradicating both exponential (FIG. 3E) and mid-stationary phase cultures (FIG. 3F), in comparison to ciprofloxacin (0.55±0.04% survival and 2.2±0.1% survival, respectively). MMC was also highly effective against biofilm cultures of *S. aureus* grown in minimal medium, eradicating cells beyond the limit of detection after 24 of treatment, compared with 18±2% survival against ciprofloxacin (FIG. 3G). MMC also killed cultures of *P. aeruginosa* PA14 grown planktonically in rich medium to exponential (FIG. 3H) and mid-stationary phase (0.0038±0.0005% survival) and in minimal medium to late-stationary phase (FIG. 3I), although the extent of killing activity was similar to that of ciprofloxacin. Therefore, MMC is significantly more effective in eradicating EHEC and *S. aureus* and on par with other antibiotics against *P. aeruginosa*, demonstrating the efficacy of MMC against several species of human pathogens.

In clinical infections, bacteria are exposed to drastically different growth conditions from those generally used within laboratory cultures. The in vitro Lubbock chronic wound pathogenic biofilm model was previously developed to closely represent growth conditions of polymicrobial infections (Y. Sun, et al., *Wound Repair Regen.* 16, 805 (2008)). We used this in vitro wound model to test MMC activity against cultures of EHEC, *S. aureus*, and *P. aeruginosa* PAO1 as well as a co-culture of *S. aureus* and *P. aeruginosa* PAO1. Our strain of *S. aureus* is coagulase-positive, causing the medium to form a jelly-like mass consisting of insoluble fibrin. Cultures were grown statically so that coagulated plasma served as a scaffold for bacterial growth in cultures containing *S. aureus*, while biofilms formed at surface interfaces served as scaffolds for bacterial growth in cultures without *S. aureus*. We found that MMC was more effective than ciprofloxacin and ampicillin against all three species under wound-like conditions in mono- and co-cultures (FIG. 4A-D). These results show that MMC is a significantly more effective treatment than other antibiotics against pathogenic strains of several species (e.g., EHEC, *S. aureus*, and *P. aeruginosa*) grown using an in vitro wound model. This substantiates the efficacy of MMC as a clinical treatment for clearing infections.

In order to test the efficacy of MMC treatment in vivo, we used an EHEC infection within the nematode *Caenorhabditis elegans*. *C. elegans* was fed on lawns of EHEC on nematode growth media (NGM) agar plates for 2 days in order to establish an infection. Nematodes were then exposed to MMC, ciprofloxacin, ampicillin, or no treatment, transferred to lawns of avirulent *E. coli* OP50, and monitored for viability. All three antibiotic treatments enhanced the survival of the EHEC-infected worms; however, survival with MMC was higher than with either ciprofloxacin or ampicillin based on four experimental replicates (10 worms per replicate) (FIG. 4E), likely because MMC eradicates persisters that can reestablish infection. Of note, we obtained similar results from four additional replicates performed with different antibiotic treatments and EHEC infection conditions. Therefore, MMC is consistently more effective than other antibiotics at clearing EHEC infection within an animal model.

Traditional antibiotics (e.g., fluoroquinolones, aminoglycosides, and β-lactams) are ineffective against persister cells due to their mechanisms which rely on cellular activity. Here, we found that MMC is highly effective because of its unique mechanism of action, which is independent of the metabolic state, by demonstrating its activity against slow-growing, non-growing, and dormant (e.g., persister and VBNC) cells, as well as its activity on cells grown planktonically, in biofilms, in an in vitro wound model, and in an in vivo animal model. In comparison, several methods have been proposed for eradicating persister cells, including increasing aminoglycoside uptake via glycolysis intermediates, altering membranes via Trp/Arg-containing antimicrobial peptides, activating ClpP-mediated self-digestion via rifampicin and ADEP4, and converting persisters to non-persisters via cis-2-decenoic acid. However, the potential application of these treatments against clinical infections is distant due to limited levels of in vivo testing. These treatments are also likely limited to a small range of species that are susceptible to the compounds. In contrast, MMC has been an FDA-approved chemotherapeutic cancer drug for over forty years with a well-characterized biochemical mechanism. Additionally, MMC passively diffuses into cells, and the DNA crosslinking activity of MMC is spontaneous, so MMC treatment should be effective against many bacterial species which cannot be fully cleared with traditional antibiotics such as recalcitrant internal and external (wound) infections.

The following materials and methods were used to obtain the results described above.

Bacterial Strains and Growth Media.

Bacterial strains and plasmids used are listed in Table 1. Experiments were conducted at 37° C. with shaking at 250 rpm unless otherwise indicated. E. coli and P. aeruginosa strains were grown in unbuffered lysogeny broth (LB) medium at pH 6.9, LB buffered with 100 mM $KPO_4$ at pH 7.0 or M9-glucose (0.4%) at pH 7.0 and S. aureus was grown in tryptic soy broth (TSB) at pH 6.8 or modified M9-glucose (0.4%) at pH 7.0 [M9-glucose (0.4%) supplemented with 0.5 mg/mL Drop-out Mix Complete w/o Yeast Nitrogen Base (USBiological, Salem, Mass., USA), 0.2 µg/mL nicotinic acid, and 0.2 µg/mL thiamine] unless otherwise indicated. Chloramphenicol (30 µg/mL) was utilized to maintain the pCA24N-based plasmids.

Minimum Inhibitory Concentration (MIC) Assay.

The MICs of MMC, ciprofloxacin, ampicillin, and gentamicin for E. coli K-12, EHEC, S. aureus, and P. aeruginosa (PA14 and PAO1) were determined by incubating freshly inoculated cultures in unbuffered LB (buffered LB for MMC and TSB for S. aureus) for 16 h with varying concentrations of each antibiotic and observing inhibition of growth based on lack of turbidity. Experiments were performed with at least two independent cultures.

Planktonic Antibiotic Killing Assays.

In order to obtain exponential and mid-stationary phase cultures in LB, buffered LB or TSB, overnight cultures (16 h) were diluted 1:1000 in fresh medium and grown to the desired turbidity (i.e., a turbidity below 2 at 600 nm for exponential phase and a turbidity of 3 to 4 at 600 nm for mid-stationary phase). Late-stationary phase cultures in LB or buffered LB were obtained by growing overnight cultures (16 h). In order to obtain exponential and late-stationary phase cultures in M9-glucose, overnight cultures (16 h) were washed diluted 1:1000 in M9-glucose and grown for the desired period of time (i.e., a turbidity of 0.4 at 600 nm for exponential phase and 24 h of growth for late-stationary phase). Anaerobically grown cultures were maintained with ~20% $CO_2$, ~79% $N_2$, and ~1% $H_2$. In order to obtain rifampicin-induced persister cultures in buffered LB, overnight cultures (16 h) were diluted 1:1000 in fresh medium and grown to a turbidity of 0.8 at 600 nm. Cultures were exposed to rifampicin (100 µg/mL) for 30 min, centrifuged, and resuspended in fresh medium to remove the rifampicin. Cultures were treated with MMC (10 µg/mL for E. coli K-12, EHEC, S. aureus, and PA14), ciprofloxacin (5 µg/mL for E. coli K-12, EHEC, S. aureus, and PA14), or gentamicin (10 µg/mL for E. coli K-12) for 3 h (unless otherwise indicated). These concentrations are at least 5×MIC to minimize survival of potential spontaneous resistant mutants. Cell viability was determined before and after antibiotic treatments by serially diluting cultures in 0.85% NaCl solution, plating 10 µL drops on LB agar, and counting colonies. Experiments were performed with at least two independent cultures.

Biofilm Antibiotic Killing Assays.

Overnight cultures (16 h) grown in LB (TSB for S. aureus) were washed and diluted to a turbidity of 0.05 at 600 nm in M9-glucose (modified M9-glucose for S. aureus) and cultures were grown for 24 h at 30° C. in 96-well plates (300 µL/well). Biofilm cultures were treated with MMC (10 µg/mL for E. coli K-12, EHEC, and S. aureus or ciprofloxacin (5 µg/mL for E. coli K-12, EHEC, and S. aureus) for 24 h. Samples were assayed before and after antibiotic treatments by carefully removing the supernatant from a well, resuspending the biofilm in 0.85% NaCl solution (adapted from Bernier et al.), triturating to break apart the biofilm, and combining the suspensions from multiple wells to obtain an averaged sample. Then cell viability was determined by serially diluting cells in 0.85% NaCl solution, plating 10 µL drops on LB agar, and counting colonies. Experiments were performed with at least two independent cultures.

Biofilm Dispersal Assay.

Overnight cultures (16 h) grown in LB were washed and diluted to a turbidity of 0.05 at 600 nm in M9-glucose and cultures were grown for 24 h at 30° C. in 96-well plates (300 µL/well). Cultures were incubated for an additional 24 h with or without MMC. Biofilm levels were assayed using crystal violet staining as described previously (Lee, et al., Appl. Environ. Microbiol. 75, 1703 (2009)). Cell growth (turbidity at 620 nm) was used to normalize the total biofilm formation (absorbance at 540 nm). Data points were averaged from 15 replicate wells using at least two independent cultures.

VBNC Antibiotic Killing Assay.

Overnight cultures (16 h) of E. coli K-12 BW25113 grown in LB were diluted 1:1000 in LB and grown to a turbidity of 3.0 at 600 nm. Cells were washed three times with 0.85% NaCl to remove nutrients and incubated in 0.85% NaCl for 32 days until the VBNC population was ~1,000-fold higher than the culturable population. VBNC cultures were treated with MMC (10 µg/mL) or ciprofloxacin (5 µg/mL) for 16 h. Samples were assayed before and after antibiotic treatments for viability of both culturable cells, determined by cell viability when plated on LB agar, and VBNC cells, determined by staining with the BacLight RedoxSensor Green Vitality Kit (Life Technologies, Carlsbad, Calif., USA). Samples (0.5 mL) were diluted 1:1 with LB to stimulate cellular respiration for 10 min prior to staining with 1 µL of 1 mM RedoxSensor™ Green dye and 1 µL of 20 mM propidium iodide. Samples were visualized in a hemocytometer (Hausser Scientific, Horsham, Pa., USA) using an Olympus BX61 confocal microscope (Olympus, Tokyo, Japan) at 200× magnification in order to determine viability of the VBNC population. Cell counting data was averaged from four images and experiment was performed with at least two independent cultures.

Quantitative Real Time Polymerase Chain Reaction (qPCR).

Overnight cultures (16 h) of E. coli K-12 BW25113/pCA24N grown in LB were diluted 1:1000 in buffered LB and grown to the desired turbidity. For exponential phase cells (i.e., non-persisters), cultures were grown to a turbidity of 2.0 at 600 nm. For rifampicin-induced persisters, cultures were grown to a turbidity of 0.8 at 600 nm, exposed to rifampicin (100 µg/mL) for 30 min, centrifuged, and resuspended in fresh medium to remove the rifampicin. Non-persister and rifampicin-induced persister cultures were treated with MMC (100 µg/mL) for 1 h. gDNA was extracted, using an UltraClean Microbial DNA Isolation Kit (MO BIO Laboratories, Carlsbad, Calif., USA), from samples taken before and after MMC treatment and 100 ng of DNA was used for qPCR of rrsG and murB using the GoTaq qPCR Master Mix (Promega, Madison, Wis., USA) and the StepOne Real-Time PCR System (Applied Biosystems, Foster City, Calif., USA) (primers are shown in Table 2). As a positive control, 3 µg of gDNA from BW25113 non-persisters was crosslinked in vitro with 500 µg/mL (1.5 mM) MMC in 0.2 mM EDTA, 50 mM NaCl, and 5 mM Tris (pH=7.6) with $Na_2S_2O_4$ added six times at 10 min intervals to reach a final concentration of 2.25 mM (1.5× molarity of MMC). The in vitro crosslinking reaction was performed anaerobically on ice and the reaction was stopped by exposure to air. Experiments were performed with at least two independent cultures.

Denaturing Agarose Gel Electrophoresis.

Overnight cultures (16 h) of *E. coli* K-12 BW25113/pCA24N grown in LB were diluted 1:1000 in buffered LB and grown to the desired turbidity. For exponential phase cells (i.e., non-persisters), cultures were grown to a turbidity of 2.0 at 600 nm. For rifampicin-induced persisters, cultures were grown to a turbidity of 0.8 at 600 nm, exposed to rifampicin (100 µg/mL) for 30 min, centrifuged, and resuspended in fresh medium to remove the rifampicin. Non-persister and rifampicin-induced persister cultures were treated with MMC (100 µg/mL) for 1 h. pDNA was extracted from samples taken before and after MMC treatment and linearized by HindIII digestion. As a positive control, 2 µg of linearized pDNA from non-persisters was crosslinked in vitro with 500 µg/mL (1.5 mM) MMC in 0.2 mM EDTA, 50 mM NaCl, and 5 mM Tris (pH=7.6) with $Na_2S_2O_4$ added six times at 10 min intervals to reach a final concentration of 2.25 mM (1.5× molarity of MMC). The in vitro crosslinking reaction was performed anaerobically on ice and the reaction was stopped by exposure to air. Linearized pDNA was visualized after electrophoresis through a TAE agarose gel and an alkaline denaturing agarose gel. Experiment was performed with at least two independent cultures.

In Vitro Wound Model.

Overnight cultures (16 h) of EHEC, *S. aureus*, and *P. aeruginosa* PAO1 were grown in LB (TSB for *S. aureus*), washed with 0.85% NaCl solution, and diluted 1:1000 (as mono-cultures or co-cultures) in wound-like medium (WLM) (45% Bolton broth, 50% heparinized bovine plasma, and 5% laked horse blood). Cultures were grown for at 37° C. without shaking for 24 h and then treated with MMC (10 µg/mL for EHEC and *S. aureus* or 15 µg/mL for *P. aeruginosa* PAO1 mono- and co-cultures), ciprofloxacin (5 µg/mL for EHEC and *S. aureus* or 10 µg/mL for PAO1 mono- and co-cultures), or ampicillin (100 µg/mL for EHEC and *S. aureus* or 2 mg/mL for PAO1 mono- and co-cultures) for 5 h. Cell viability was determined before and after antibiotic treatments by serially diluting cultures in 0.85% NaCl solution, plating 10 µL drops on LB agar, and counting colonies. Samples containing *S. aureus* were coagulated, so sections of coagulated WLM were cut and weighed add appropriate amounts of antibiotics. Coagulated samples were triturated and vortexed to release cells prior to measuring cell viability. Experiments were performed with at least two independent cultures.

*C. elegans* Animal Model.

*C. elegans* Bristol N2 was maintained using standard practices. Growth of *C. elegans* was synchronized by isolating eggs from gravid adults, hatching the eggs overnight in M9-buffer, and plating the $L_1$-stage worms onto lawns of *E. coli* OP50 on nematode growth medium (NGM) agar plates. Nematodes were grown to young adults at 25° C. and transferred (10 worms per plate) to lawns of EHEC or *E. coli* OP50 as a negative control. After feeding on EHEC for 2 days, nematodes were suspended in 20% NGM and 80% M9-buffer at pH 6.0 and exposed to MMC (10 µg/mL), ciprofloxacin (5 µg/mL), ampicillin (100 µg/mL) or no treatment for 6 h. After antibiotic treatment, worms were plated on lawns of *E. coli* OP50 and viability was scored daily. Experiment was performed with at least four replicate plates.

TABLE 1

Bacterial strains and plasmids used in this Example.

| | Genotype | Source |
|---|---|---|
| Strain | | |
| *E. coli* K-12 BW25113 | rrnB3 ΔlacZ4787 hsdR514 Δ(araBAD)567 Δ(rhaBAD)568 rph-1 | (T. Baba, et al.) |
| *E. coli* K-12 BW25113 ΔuvrA | BW25113 ΔuvrA Ω $Km^R$ | (T. Baba, et al.) |
| *E. coli* K-12 BW25113 ΔuvrB | BW25113 ΔuvrB Ω $Km^R$ | (T. Baba, et al.) |
| *E. coli* K-12 BW25113 ΔuvrC | BW25113 ΔuvrC Ω $Km^R$ | (T. Baba, et al.) |
| EHEC 86-24 | EHEC O157:H7 Stx2+ | (Sperandio) |
| *E. coli* OP50 | *E. coli* B strain (uracil auxotroph) | (S. Brenner) |
| *S. aureus* ATCC 29213 | Antibiotic-susceptible reference strain | ATCC |
| *P. aeruginosa* PAO1 | Wild-type strain | (M. A. Jacobs et) |
| *P. aeruginosa* PA14 | Wild-type strain | (N. T. Liberati et al.) |
| Plasmid | | |
| pCA24N | $Cm^R$; $lacI^q$, pCA24N | (M. Kitagawa et al.) |
| pCA24N-uvrA | $Cm^R$; $lacI^q$, pCA24N $P_{T5-lac}$::uvrA | (M. Kitagawa et al.) |

M. Kitagawa et al., DNA Res. 12, 291 (2005)
S. Brenner, Genetics 77, 71 (1974)
T. Baba et al.,. Mol. Syst. Biol. 2, 2006.0008 (2006
Sperandio, A. G. et al. J. Bacteriol. 183, 5187 (2001)
M. A. Jacobs et al., Proc. Natl. Acad. Sci. U.S.A. 100, 14339 (2003).
N. T. Liberati et al., Proc. Natl. Acad. Sci. U.S.A. 103, 2833 (2006)

TABLE 2

Oligonucleotides used for qPCR.

| Primer name | Sequence (5'→3') |
|---|---|
| rrsG-RT-F | TATTGCACAATGGGCGCAAG (SEQ ID NO: 1) |
| rrsG-RT-R | ACTTAACAAACCGCCTGCGT (SEQ ID NO: 2) |
| murB-RT-F | GAACAACAATTACTCAATGCCTGGCAGTATGC (SEQ ID NO: 3) |

TABLE 2-continued

Oligonucleotides used for qPCR.

| Primer name | Sequence (5'→3') |
|---|---|
| murB-RT-R | CCATAAGCACCAATATTCTGGATAGGTGATGAGC (SEQ ID NO: 4) |

"F" indicates forward primers and "R" indicates reverse primers.

TABLE 3

Summary of qPCR results. The cycle number ($C_t$) for each sample is indicated for the target genes (rrsG and murB) for samples before and after MMC crosslinking, performed in vivo (persisters and non-persisters) and in vitro. Fold changes in amplifiable DNA were calculated using:
$$2^{-(C_{t\,after\,MMC} - C_{t\,before\,MMC})}$$
The specificity of the qPCR products were verified by melting curve analysis. Means and standard deviations are indicated (n = 2).

| Condition | $C_t$ (before MMC) | $C_t$ (after MMC) | Fold Change |
|---|---|---|---|
| Persisters | | | |
| rrsG | 8.41 ± 0.72 | 10.74 ± 1.10 | −5.01 ± 0.51 |
| murB | 12.41 ± 1.14 | 15.00 ± 1.24 | −5.99 ± 0.50 |
| Non-persisters | | | |
| rrsG | 8.00 ± 0.87 | 10.57 ± 0.35 | −5.95 ± 0.20 |
| murB | 11.85 ± 0.90 | 14.20 ± 0.39 | −5.13 ± 0.14 |
| In vitro crosslinked | | | |
| rrsG | 6.98 ± 0.08 | 17.48 ± 0.01 | −1456 ± 1 |
| murB | 10.52 ± 0.41 | 21.18 ± 0.37 | −1621 ± 28 |

Example 2

This Example demonstrates that cisplatin is capable of eradicating persister cells which cannot be killed by traditional antibiotics.

Cisplatin (cis-diamminodichloroplatinum(II), FIG. 7 inset) is an FDA-approved drug that has been used to treat testicular, ovarian, bladder and head and neck cancers. The biological effects of complexes of platinum were found serendipitously in 1965 in an electrophoresis study where platinum from an electrode was found to inhibit cell division and increase *Escherichia coli* cell length by as much as 300 fold (Rosenberg B, et al. Nature 205:698-699). Like MMC, cisplatin crosslinks DNA but the crosslinks occur primarily on the same strand of DNA with intra-strand crosslinks between purines at adjacent guanines (54 to 65%), at AG sequences (17 to 19%), and at GNG sequences where N can be any nucleotide (<8%) (Eastman 1987).

In this Example we demonstrate that cisplatin is effective against persister cells in a broad range of bacteria including commensal *E. coli* K-12 as well as pathogenic strains of *E. coli*, *Staphylococcus aureus* (frequently found in wounds), and *Pseudomonas aeruginosa* (including clinical, multi-drug resistant strains). We also demonstrate that cisplatin eradicates persister cells more effectively than MMC. Therefore, cisplatin has broad-spectrum activity against growing, non-growing, and persister cells, and has potential for use in the treatment of recalcitrant infections.

The following materials and methods were used to obtain the data presented in this Example.

Bacterial strains and growth media. The bacterial strains and plasmids used are listed in Table 4. Bacterial strains were grown at 37° C. with shaking at 250 rpm. *E. coli* and *P. aeruginosa* were grown in lysogeny broth (LB) at pH 6.9 or M9-glucose (0.4%) at pH 7.0 (Rodriguez and Tait 1983), and *S. aureus* was grown in tryptic soy broth (TSB) at pH 6.8. Kanamycin was added at 50 µg/mL for the *E. coli* isogenic mutants and 15 µg/mL gentamicin was used for the *P. aeruginosa* isogenic mutants.

Stocks of cisplatin (2 mg/mL, Sigma-Aldrich, St. Louis, Mo., USA) were prepared in 0.1M NaClO4 and MMC (0.5 mg/mL, Fisher Scientific, Pittsburgh, Pa., USA) was prepared in water. Stocks of busulfan (2 mg/mL, Cayman Chemical, Ann Arbor, Mich., USA), melphalan (2 mg/mL, Cayman Chemical), dynemicin A (5 mg/mL, AdooQ, Irvine, Calif., USA), and tirapazamine (0.5 mg/mL, Sigma-Aldrich) were prepared in dimethylsulfoxide, the stock of cyclophosphamide (0.5 mg/mL, Cayman Chemical) was prepared in water, and the stock of carmustine (214 mg/mL, Enzo Life Sciences, Farmingdale, N.Y., USA) was prepared in ethanol.

Minimum inhibitory concentration (MIC) assay. To determine the MICs of cisplatin for *E. coli* K-12, enterohemorrhagic *E. coli* (EHEC), *S. aureus*, and *P. aeruginosa* (PAO1 and PA14), freshly inoculated cultures (at least two independent cultures) in buffered LB (TSB for *S. aureus*) were incubated for 16 h with varying concentrations of cisplatin, and growth inhibition was assayed by the lack of turbidity.

Persister cell killing and eradication assays (planktonic cells). For the time course experiment, late stationary phase cells of *E. coli* K-12 (wild-type and isogenic mutants) were prepared by growing cells overnight (16 h) in LB medium buffered with 100 mM KPO4 at pH 7.0 (buffered LB). A 1 mL culture was used for a drop (10 µL×3) assay to check cell viability at 0 h (i.e., before antibiotic treatment). An 18 mL culture was treated with ciprofloxacin (5 µg/mL, for the wild-type strain) and cisplatin (500 µg/mL) for 8 h (250 mL flask, 250 rpm). The concentrations of ciprofloxacin and cisplatin were at least 5×MIC to minimize survival of potential spontaneous resistant mutants. At 1 h intervals, 1 mL culture was centrifuged at 10,000 rpm for 3 min, the supernatant was discarded, the cells were resuspended in 1 mL of normal saline (0.85% NaCl), and the cell suspension was serially diluted for a drop assay to check cell viability. Experiments were performed with at least two independent cultures.

To test for eradication, the wild-type *E. coli* K-12 cells were treated with cisplatin for 12 h, a 1 mL sample was centrifuged, the cell pellet was resuspended in 150 µL of normal saline, and the cells were spread on LB agar to check cell viability. Another 1 mL culture was diluted 1:10 with fresh buffered LB and the cells were incubated to allow any remaining cells to replicate. After 12 h, 18 h, and 24 h, 1 mL samples were centrifuged, resuspended in 150 µL of normal saline and spread on LB agar plates to check cell viability. At least two independent cultures were used.

Rifampicin-pretreatment was used to convert nearly all the *E. coli* exponentially-growing cells to persister cells. In brief, overnight cultures (16 h) of *E. coli* BW25113 were diluted 1:1000 in buffered LB and grown to a turbidity of 0.8 at 600 nm (250 mL flask, 250 rpm). Cultures were treated with rifampicin (100 µg/mL) for 30 min (250 mL flask, 250 rpm), centrifuged, and resuspended in fresh medium to remove the rifampicin. A 1 mL culture was used for a drop assay to check cell viability at 0 h. A 5 mL culture was treated with ciprofloxacin (5 µg/mL), cisplatin (500 µg/mL) or equivalent amount of 0.1M NaClO4 (as a solvent control for cisplatin) for 3 h (125 mL flask, 250 rpm). After 3 h, 1 mL of culture was centrifuged at 10,000 rpm for 3 min, the supernatant was discarded, the cells were resuspended in 1 mL of normal saline, and the cell suspension was serially diluted for a drop assay to check cell viability. In addition, 1 mL samples were centrifuged, and the cell pellet resuspended in 150 μL of normal saline and spread on LB agar. Experiments were performed with at least two independent cultures.

To test whether lower concentrations than 500 μg/mL of cisplatin generate resistant mutants, 5 mL cultures of rifampicin-induced persister cells were treated with 200 μg/mL of cisplatin and cells were enumerated by the drop assay using LB agar, LB agar with 200 μg/mL of cisplatin (LBCP200), and LB agar with 500 μg/mL of cisplatin (LBCP500). Experiments were performed with at least two independent cultures.

For the persister cell assay of the pathogens, stationary-phase cells were used. Cultures of EHEC, *P. aeruginosa*, and *S. aureus* were prepared by a 1:1000 dilution of overnight grown cultures (LB medium for EHEC and *P. aeruginosa*, TSB for *S. aureus*) into fresh buffered LB medium for EHEC, M9-glucose for *P. aeruginosa*, and TSB for *S. aureus* and re-growing the cells to a turbidity of 3 to 4 at 600 nm for EHEC and *S. aureus* and growing for 24 h for *P. aeruginosa*. Stationary-phase cultures of EHEC (buffered LB medium), *P. aeruginosa* (M9-glucose medium), and *S. aureus* (TSB medium) were then treated with cisplatin (500 μg/mL for EHEC and *S. aureus*, 250 μg/mL for *P. aeruginosa*) for 3 h (250 mL flask, 250 rpm).

To compare the killing efficiency of cisplatin with MMC, stationary-phase cells of *P. aeruginosa* PA14 in M9-glucose (24 h) were treated with 1× and 5×MIC of cisplatin (50 μg/mL and 250 μg/mL, respectively) or 1× and 5×MIC of MMC (2 μg/mL and 10 μg/mL, respectively) for 3 h. $NaClO_4$ (0.1M) was used as a solvent control. The viability of the cells was determined before and after cisplatin and MMC treatment. At least two independent cultures of each strain were used in each experiment.

Persister cell killing assay (biofilm cells). Overnight (16 h) grown cultures in LB were diluted to a turbidity of 0.05 at 600 nm in M9-glucose and cultures were grown for 24 h at 37° C. in 96-well plates (250 μL/well). Biofilm formation was assayed using the crystal violet staining method (Fletcher 1977) and was normalized by planktonic cell growth (turbidity at 620 nm) to account for any differences in growth rates. Data were averaged from 6 replicate wells using at least two independent cultures. Biofilm cultures were treated for 3 h with 1× and 5× MIC of MMC (2 μg/mL and 10 μg/mL, respectively) and 1× and 5×MIC cisplatin (50 μg/mL and 250 μg/mL, respectively). $NaClO_4$ (0.1M) was used as a solvent control for cisplatin. Cell viability in biofilms was assayed before and after the MMC and cisplatin treatments by removing supernatants (planktonic cells) from each well carefully, resuspending the biofilm in normal saline, and sonicating twice at 3W for 10 sec (Ueda and Wood 2009) to break apart the biofilm cells (due to the aggregative nature of *P. aeruginosa* ΔtpbA cells). Suspensions from multiple wells were combined to get an averaged sample. Then the cell suspensions were serially diluted in normal saline for a drop assay to check cell viability. Experiments were performed with at least two independent cultures.

Validation of persisters. To validate that the persister cells are tolerant to antibiotics, not spontaneous resistant mutants, three rounds of the persister assay were performed. Overnight (16 h) cultures of *E. coli* BW25113 were diluted 1:1000 with fresh buffered LB and grown to a turbidity of ~0.8 at 600 nm. A 1 mL culture was used for the drop assay, and a 5 mL culture was treated with ciprofloxacin (5 μg/mL) and ampicillin (100 μg/mL) for 3 h (125 mL flask, 250 rpm). After the first round of antibiotic treatment, a 1 mL sample was centrifuged at 10,000 rpm for 3 min, and the cells were resuspended in 1 mL of normal saline. A 100 μL of cell suspension was used for the drop assay on both LB and LB with 5 μg/mL of ciprofloxacin (LBCipro5) agar (for ciprofloxacin treated samples) or LB with 100 μg/mL of ampicillin (LBAmp100) agar (for ampicillin treated samples). For the second and third rounds, cell suspensions were diluted 1:100 with fresh buffered LB and regrown to a turbidity of ~0.8 at 600 nm and used for antibiotic treatment followed by the drop assay. Experiments were performed with at least two independent cultures.

Using the foregoing materials and methods for this Example, the following results were obtained.

Cisplatin eradicates *E. coli* K-12 persister cells. In this Example we tested seven other DNA crosslinking compounds: busulfan (100 μg/mL), carmustine (100 μg/mL) cisplatin (100 μg/mL), cyclophosphamide (100 μg/mL), dynemicin A (200 μg/mL), melphalan (100 μg/mL), and tirapazamine (10 μg/mL). Of these, only cisplatin exhibited antimicrobial activity for *E. coli* K-12 cells, so we focused on this compound.

To evaluate the effectiveness of cisplatin against persister cells, cisplatin was compared with ciprofloxacin, a fluoroquinolone which inhibits DNA replication and kills both growing and non-growing cells but not persister cells and which is commonly used in persister studies (Conlon et al., Nature 503:365-370). Therefore, in this Example, ciprofloxacin tolerance represents the baseline level of persistence with an effective antibiotic. Additionally, antibiotic treatments were at least 5× the minimum inhibitory concentration for *E. coli* (MIC, 100 μg/mL for cisplatin, Table 5, and 0.05 μg/mL for ciprofloxacin to ensure eradication of non-persisters and to minimize the survival of potential spontaneous resistant mutants.

As in Example 1, we demonstrated ciprofloxacin tolerance is due to persistence rather than spontaneous genetic resistance; hence, ciprofloxacin tolerance is an indicator of persistence. To validate again that persister cells were generated, we performed three rounds of the persister assay with ciprofloxacin (100×MIC, 5 μg/mL) as well as with ampicillin at 100 μg/mL [10×MIC, MIC for ampicillin is 10 μg/mL, since persister cells have different tolerances to different antibiotics. We found there was no significant increase in *E. coli* K-12 cell viability after both ciprofloxacin or ampicillin treatments: the survival rates for ciprofloxacin were 0.045±0.008%, 0.03±0.01%, and 0.012±0.002% after rounds 1, 2, and 3, respectively and the survival rates for ampicillin were 0.001±0.001%, 0.0001±0.0000%, and 0.0001±0.0000% after rounds 1, 2, and 3, respectively. Moreover, no colonies were detected on either LBCipro5 or LBAmp100 agar, which confirmed that no resistant mutants were generated.

Initially, we tested whether cisplatin kills late stationary phase (16 h of growth) cells of *E. coli* K-12 in a time course experiment, since persister levels are high at this growth stage. We found that cisplatin (500 μg/mL, 5×MIC) nearly eradicated these cells; however, ciprofloxacin, at a much higher MIC (5 μg/mL, 100×MIC) had little activity against the persister cells (FIG. 7).

Figure 1:
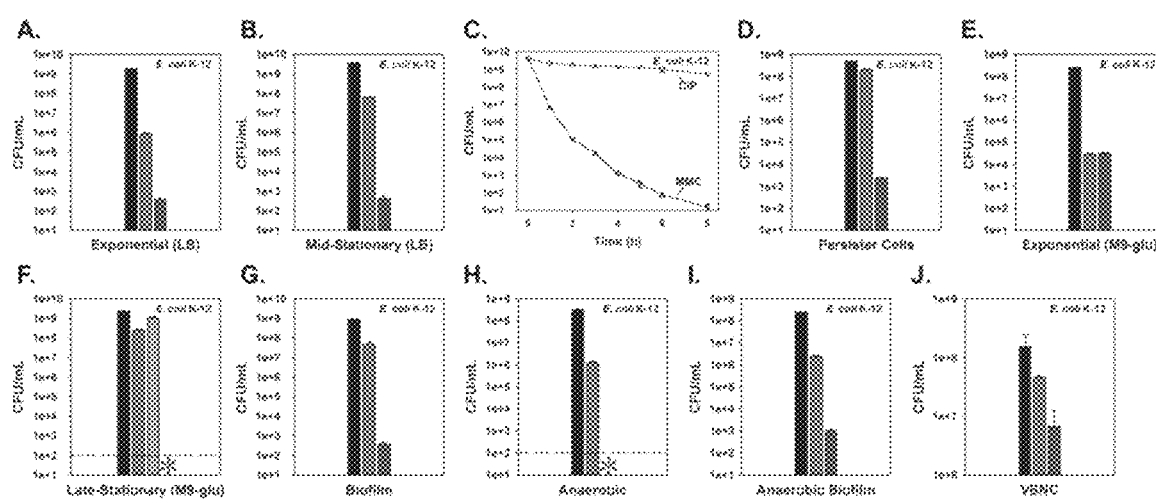
FIG. 1: MMC eradicates metabolically dormant *E. coli* K-12 cells in suspension and in biofilms. Cell viability for exponential (A) and mid-stationary phase (B) cultures in buffered LB. (C) Time course of killing of late stationary-phase cells in buffered LB. (D) Cell viability of rifampicin-induced persister cultures in buffered LB. Cell viability of exponential (E) and late-stationary phase cultures (F) in M9-glucose. Cell viability of biofilm cultures in M9-glucose (G), anaerobic late-stationary phase cultures in LB (H), anaerobic biofilm cultures in M9-glucose (I), and VBNC cultures (J). Cell viability is shown before (black/left bar in each panel and after treatment with ciprofloxacin (green/middle bar in each panel), gentamicin (purple/right bar in panel F only), and MMC (red, right bar in each panel except F and H, where * represents eradication beyond the limit of detection by MMC. Means±s.d. are shown throughout (n≥2). MMC is mitomycin C and CIP is ciprofloxacin.

We also tested two isogenic *E. coli* K-12 catalase mutants katE and katG to investigate whether cisplatin works via the production of reactive oxygen species (ROS). We did not find any significant differences in killing of the katE or katG mutants compared to the wild-type strain after prolong (8 h) treatment with 5×MIC of cisplatin (FIG. 1). Hence, reactive oxygen species do not seem to play a role in killing by cisplatin.

We also tested whether cisplatin completely eradicates *E. coli* K-12 persister cells and abolishes regrowth when cisplatin is withdrawn. We found that treatment with 5×MIC of cisplatin for 12 h completely eradicated *E. coli* persister cells since there were no colonies from 1 mL of culture, and there was no increase in turbidity or colonies (from 1 mL sample) when 1 mL of the cisplatin-treated culture was used to inoculate fresh medium and the medium was incubated for 12 h, 18 h, and 24 h.

Next, we tested cisplatin using persister cells of *E. coli* K-12 prepared by pretreating with rifampicin. We found that after 3 h, ciprofloxacin (5 µg/mL, 100×MIC) was unable to kill 9±1% of the persister cells; however, cisplatin (500 µg/mL, 5×MIC) reduced the number of persister cells below the limit of detection (100 cells/mL for drop assay) (FIG. 8A). To investigate further the number remaining cells after the 3 h cisplatin treatment, 1 mL samples were plated and found to produce 37±5 colonies; hence, the surviving fraction was 0.00001±0.00000%. Sodium perchlorate (NaClO4) was used as the solvent for cisplatin since dimethylsulfoxide inactivates cisplatin (Hall et al. 2014), and NaClO4 did not show any killing effect (data not shown). Hence, cisplatin is highly effective against *E. coli* persister cells.

The use of lower concentrations than 5×MIC (500 µg/mL) of cisplatin was also tested to see if this generates any spontaneous resistant mutants. We found that treatment with 2×MIC (200 µg/mL) of cisplatin yields 0.08% survivors on LBCP200 agar plates, however, no colonies were found on LBCP500 agar plates. To confirm that the lack of colonies on the LBCP500 agar plates was not due to limits of detection of the drop assay (100 cells/mL), all the colonies from the LBCP200 agar plates were streaked on LBCP500 agar plates. However, no growth was observed. Similarly, none of the cells that survived from 3 h treatments with 5×MIC of cisplatin (1 mL spread counts) grew on LBCP500 agar plates. Therefore, treatment with 2× and 5×MIC of cisplatin does not generate spontaneous resistant mutants in these experiments.

Cisplatin eradicates pathogenic persister cells. Since MMC as an anticancer drug possesses broad spectrum activity against various bacterial pathogens as demonstrated in Example 1, and since cisplatin is also an anticancer drug, we tested whether cisplatin can kill diverse bacterial pathogens. We used stationary-phase cells since persister levels are high at this growth stage (Lewis K. Persister cells, dormancy and infectious disease. (2007) Nat Rev Microbiol 5:48-56) and conditions have not been devised yet to convert these cells to persister cells using chemical pre-treatments as with *E. coli* K-12 (Kwan B W, et al. Antimicrob Agents Chemother 57:1468-1473).

We found that cisplatin (500 µg/mL, 5×MIC) eradicated stationary-phase cells of enterohemorrhagic *E. coli* (EHEC), a common *E. coli* pathogen associated with food-borne illness in humans (FIG. 8B). Cisplatin was also tested against the Gram-negative opportunistic pathogen *P. aeruginosa* PA14, and cisplatin (250 µg/mL, 5×MIC) eradicated stationary-phase cells of PA14 (FIG. 8C). Similar results were obtained using the related strain *P. aeruginosa* PA01 (data not shown). Furthermore, cisplatin at 100 µg/mL (0.25×MIC or 1×MIC, Table 5) nearly eradicated the persister cells of four clinical strains of *P. aeruginosa* (isolated from adult pneumonia patients and pediatric cystic fibrosis patients) which are resistant to multiple (12 to 18) antibiotics (Table 4), and one of them, INP-57M, is resistant to the canonical quorum sensing quenching agent furanone C-30 (Garcia-Contreras R, et al. 2015. Pathog Dis 73:ftv040); with cisplatin, there were 0.02±0.03%, 0.05±0.06%, 0.01±0.00%, and 0.02±0.00% survival for strains RME-101, INP-37, INP-57M, and INP-64M, respectively.

We also tested the effectiveness of cisplatin with a methicillin-sensitive strain of the Gram-positive human pathogenic bacterium *S. aureus* ATCC29213 and two clinical isolates from diabetic food patients. Cisplatin (500 µg/mL, 1.7×MIC) nearly eradicated (0.0001±0.0001% survival) stationary phase cells of *S. aureus* ATCC29213 (FIG. 8D). Similarly, the stationary-phase cells of both clinical isolates were severely affected by 500 µg/mL of cisplatin (2.5±3.5% survival and 10±4% survival for the isolates 5B and 50F, respectively) and a higher concentration (800 µg/mL) was able to completely eradicate these cells. Together these results show that cisplatin is capable of eradicating the persister cells of three pathogens.

Cisplatin is more effective than MMC with *P. aeruginosa*. Previously, we found that MMC was not effective in eradicating stationary-phase cells of *P. aeruginosa* PA14, and MMC was about as effective as ciprofloxacin with planktonic cells of this strain as shown in Example 1. Hence, we compared the efficacy of cisplatin and MMC at 1×MIC (50 µg/mL for cisplatin [Table 5] and 2 µg/mL for MMC and at 5×MIC (250 µg/mL for cisplatin and 10 µg/mL for MMC). As observed in Example 1, MMC failed to eradicate stationary phase cells of PA14 (5±2% survival for 1×MIC and 0.0056±0.0004% survival for 5×MIC); however, even 1×MIC of cisplatin completely eradicated PA14 persister cells (FIG. 9A). Similar results were obtained with *P. aeruginosa* strain PA01 (data not shown). Therefore, cisplatin is a more effective than MMC in killing the persister cells of bacterial pathogens.

We then tested the efficacy of cisplatin vs. MMC using biofilm cells of *P. aeruginosa*, since levels of persisters are also high in biofilms (Lewis K. 2008. Curr Top Microbiol Immunol 322:107-131), and they are a major cause of bacterial infections (Wolcott R, Dowd S. 2011. Plast Reconstr Surg 127:28S-35S). We utilized the ΔtpbA mutant of *P. aeruginosa* since it produces substantially more biofilm than PA14 due to elevated levels of cyclic diguanylate (Ueda A, Wood T K. (2009) PLoS Pathog. 5:e1000483); this elevated biofilm formation was confirmed since the ΔtpbA mutant produced 6-fold more biofilm than PA14 in M9-glucose medium (FIG. 9B). We then treated biofilm cultures of PA14 and its ΔtpbA mutant with 5×MIC of cisplatin (250 µg/mL), and compared these results with those of treatment with 5×MIC of MMC (10 µg/mL). Cisplatin completely eradicated (beyond the limit of detection, 100 cells/mL) the biofilm cells of ΔtpbA and those of PA14. However, MMC could not eradicate biofilms of either strain (FIG. 9C). These results clearly demonstrate that cisplatin is more potent than MMC with *P. aeruginosa*.

FIG. 10 provides data obtained from analysis of in vitro crosslinking of DNA with cisplatin and denaturing agarose gel electrophoresis. To produce the results shown in FIG. 10, pCA24N DNA (4518 bp) was in vitro crosslinked with cisplatin following a standard protocol. In brief, 2.2 µg of pCA24N DNA was linearized by HindIII digestion and cleaned using Wizard-SV gel and PCR clean-up system (Promega, Madison, Wis., USA). Linearized pCA24N was then treated with 200 µM (60 µg/mL) of cisplatin (Sigma-Aldrich, St. Louis, Mo., USA) for 1.5 h and 3.5 h at 37° C. The same amount of pCA24N DNA was also treated with an equivalent amount of 0.1M NaClO4 (solvent control for cisplatin) for 3.5 h at 37° C. Mitomycin C (MMC) was used as a positive control to compare types of crosslinking between cisplatin and MMC. For MMC, the same amount (2.2 µg) of pCA24N DNA was crosslinked essentially as in Example 1. In brief, linearized pCA24N DNA was treated with 500 µg/mL (1.5 mM) MMC or without MMC in 0.2 mM EDTA, 50 mM NaCl, and 5 mM Tris (pH 7.6) with Na2S2O4 added six times at 10 min intervals to reach a final concentration of 2.25 mM (1.5×molarity of MMC). The crosslinking reaction with MMC was performed anaerobically on ice and the reaction was stopped by exposure to air. Finally, cisplatin or MMC treated pCA24N DNA was visualized after electrophoresis through a 1% alkaline denaturing agarose gel that creates single-stranded DNA.

As we enter the post-antibiotic age, finding suitable alternatives to combat recalcitrant infections is mandatory. Hence, repurposing pharmaceuticals that are in current clinical use is an attractive strategy since it potentially saves time and resources and may benefit numerous patients. For example, after screening 5850 P. aeruginosa transposon mutants, we identified that uracil is a cell signal that increases biofilm formation and demonstrated that the anticancer drug 5-fluorouracil is effective in inhibiting biofilm formation (Ueda et al. 2009). Remarkably, clinical trials in humans demonstrated that coating with 5-fluorouracil was useful to prevent colonization and biofilm formation in central venous catheters, being even more effective than the positive control (chlorhexidine-silver-sulfadiazine) (Walz J M, et al., (2010) Crit Care Med 38:2095-2102). Given that cisplatin is also an FDA-approved, anti-cancer agent, our results here strongly support the repurposing of for use in killing persister cells.

It is established now that chronic infections are facilitated by the survival of a small percentage of dormant persister cells (Fauvart M, et al. (2011) J Med Microbiol 60:699-709), and since current antimicrobial agents target growth processes such as cell wall replication and protein and DNA synthesis, currently there are no drugs in clinical use that target persister cells. To address this need to combat persister cells, we demonstrated that MMC is effective for the eradication of persister cells in Example 1. In this Example, our results demonstrate that cisplatin is also highly effective in treating persister cells. We show that cisplatin can eradicate the persister cells formed from E. coli, EHEC, and P. aeruginosa (FIGS. 7 and 8). We also found that cisplatin was highly effective against S. aureus and P. aeruginosa clinical strains. Hence it is effective against Gram-negative and Gram-positive bacteria that are among the most common causes of nosocomial infections. Furthermore, our results indicate that cisplatin is more effective than MMC with P. aeruginosa for both biofilm and planktonic cells (FIG. 9). This is the first demonstration showing cisplatin is highly effective in treating dormant persister cells.

Since P. aeruginosa biofilm persister cells were eradicated, cisplatin may be effective for treating wounds where biofilms are commonly formed from P. aeruginosa and S. aureus (DeLeon S, et al. (2015) Infect Immun 82:4718-4728). This is important since wound care in the U.S. costs $18 B/yr, and over 200,000 people die each year from wounds that do not heal properly (DeLeon et al., 2014).

Of the seven anticancer drugs tested for this Example, only cisplatin showed potent anti-persister activity. The efficacy of cisplatin may be influenced by a number of factors, including that along with busulfan, carmustine, melphalan, and dynemicin, cisplatin is a direct alkylating agent. Of these direct alkylating agents, cisplatin is the only one that contains a metal; hence, its enhanced activity may also be related to the creation of ROS. However, we found here that catalase mutants of both E. coli and P. aeruginosa are not more susceptible to cisplatin. Therefore, the mechanism of killing persister cells by cisplatin direct crosslinking of DNA that is independent of cell metabolism, which allows it to work on metabolically-dormant persister cells. We also reconfirmed that cisplatin indeed crosslinks the same strand of DNA (FIG. 10).

While the invention has been described through specific embodiments, routine modifications will be apparent to those skilled in the art and such modifications are intended to be within the scope of the present invention.

What is claimed is:

1. A method for reducing bacterial persister cells and/or dormant viable but non-culturable (VBNC) cells in a bacterial population, the method comprising administering an effective amount of cisplatin to the population such that a reduction in the bacterial persister cells and/or the VBNC cells in the population occurs, and optionally also administering Mitomycin C to the population, wherein the persister cells and/or VBNC cells are in a stationary growth phase.

2. The method of claim 1, wherein the reduction of the persister cells and/or the VBNC cells is greater than a reference, wherein the reference comprises a value obtained from reducing persister cells and/or or reducing VBNC cells of the same bacterial species using a matched amount of one of ciprofloxacin, ampicillin, or gentamicin.

3. The method of claim 1, wherein the bacterial persister cells and/or VBNC cells are eradicated from the population.

4. The method of claim 1, wherein the persister cells and/or VBNC cells are resistant to one or more antibiotics.

5. The method of claim 1, wherein the persister cells and/or VBNC cells are present in anaerobic conditions.

6. The method of claim 1 wherein the bacterial persister cells are reduced.

7. The method of claim 2, wherein the bacterial persister cells comprise pathogenic Gram-negative bacteria.

8. The method of claim 7, wherein the bacterial persister cells comprise pathogenic Gram-positive bacteria.

9. The method of claim 1, wherein the pathogenic bacterial persister cells comprise *S. aureus, P. aeruginosa*, or *E. coli*.

10. The method claim 1, wherein the population is present in an infection in a wound of an individual.

11. The method of claim 10, wherein the infection in the wound comprises pathogenic bacteria that are resistant to one or more antibiotics that are not mitomycin C.

12. The method of claim 1, wherein the population comprises an infection in an individual, wherein the individual has been previously diagnosed with a bacterial infection and has been treated with at least one antibiotic other than mitomycin C and wherein the diagnosed bacterial infection was not cleared by the previous treatment.

13. The method of claim 12, wherein the diagnosed bacterial infection comprises antibiotic resistant bacteria.

14. The method of claim 1, wherein culturable pathogenic bacterial cells in the population are eradicated.

15. The method of claim 1, wherein the population is comprised by a biofilm.

16. The method of claim 1, wherein the bacterial persister cells and/or VBNC cells are reduced or eradicated, but the biofilm is not dispersed.

17. The method of claim 1, wherein the population comprises the persister cells, and wherein the entire population of persister cells is eradicated.

18. The method of claim 17, wherein the population comprises persister cells that are resistant to at least one antibiotic.

19. The method of claim 1, wherein the Mitomycin C is also administered.

* * * * *